United States Patent
Stergiopoulos et al.

(10) Patent No.: US 6,535,570 B2
(45) Date of Patent: Mar. 18, 2003

(54) METHOD FOR TRACING ORGAN MOTION AND REMOVING ARTIFACTS FOR COMPUTED TOMOGRAPHY IMAGING SYSTEMS

(75) Inventors: Stergios Stergiopoulos, Toronto (CA); Amar C. Dhanantwari, North York (CA)

(73) Assignee: Her Majesty the Queen in right of Canada, as represented by the Minister of National Defence of Her Majesty's Canadian Government, Ottawa (CA)

( * ) Notice: Subject to any disclaimer, the term of this patent is extended or adjusted under 35 U.S.C. 154(b) by 170 days.

(21) Appl. No.: 09/773,925

(22) Filed: Feb. 2, 2001

(65) Prior Publication Data

US 2002/0025017 A1 Feb. 28, 2002

Related U.S. Application Data

(63) Continuation-in-part of application No. 09/334,640, filed on Jun. 17, 1999, now Pat. No. 6,236,705.

(51) Int. Cl.$^7$ ................................................ A61B 6/03
(52) U.S. Cl. .............................. 378/8; 378/15; 378/901
(58) Field of Search ........................... 378/4, 8, 15, 901

(56) References Cited

U.S. PATENT DOCUMENTS

| | | | | |
|---|---|---|---|---|
| 4,635,293 A | * | 1/1987 | Watanabe | 382/44 |
| 4,870,692 A | * | 9/1989 | Zuiderveld et al. | 382/6 |
| 6,236,705 B1 | * | 5/2001 | Stergiopoulos et al. | 378/8 |
| 2002/0025017 A1 | * | 2/2002 | Stergiopoulos et al. | 378/8 |

OTHER PUBLICATIONS

Stergiopoulos, "Implementation of Adaptive and Synthetic–Aperture Processing Schemes in Integrated Active–Passive Sonar Systems", Proceedings of the IEEE, vol. 86, No. 2, Feb. 1998, pp. 358–396.

Stergiopoulos, "Limitations on towed–array gain imposed by a nonisotropic ocean", J. Acoust. Soc. Am. 90 (6), Dec. 1991, pp. 3161–3172.

* cited by examiner

*Primary Examiner*—David V. Bruce
(74) *Attorney, Agent, or Firm*—Larson & Taylor, PLC

(57) ABSTRACT

A method of tracking organ motion and removing motion artifacts in conventional computer tomography scans is disclosed. Sensor time series indicative of projection measurement data of the object are correlated using a software spatial overlap correlator method in order to obtain a sinogram indicative of organ motion. The software spatial overlap correlator method is based on the fact that the image sampling process of a computer tomography scanner is periodical, therefore, image samples taken at a time t and at a time t+T are taken from identical spatial locations. The sinogram is then processed using a retrospective gating method or a coherent sinogram synthesis method in order to correct the image data for motion effects. This method for motion correction is software based and, therefore, can be easily implemented in existing computer tomography systems without major hardware modification.

18 Claims, 29 Drawing Sheets

Image Reconstruction Motion Artifacts

Tracking Of Organ Motion

Removal of motion artifacts Using Adaptive Processing

Slice of Sensor # 96
No Motion

Sensor with Motion Present

Motion Isolated (Expanded x 2)

Snapshots 1,5,10,15,10; Sensor #96; mu + 0.25

Figure 12a                    Figure 12b

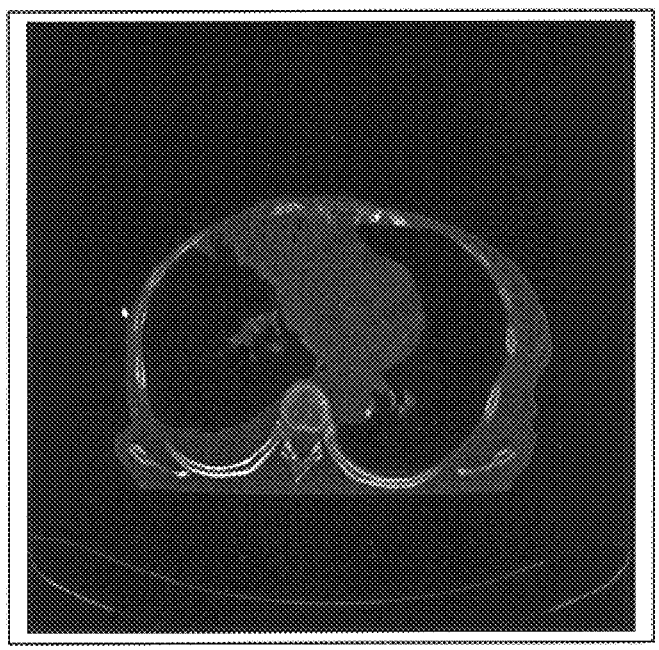
Figure 26   Output of conventional CT scanner for a human patient following free-breath.

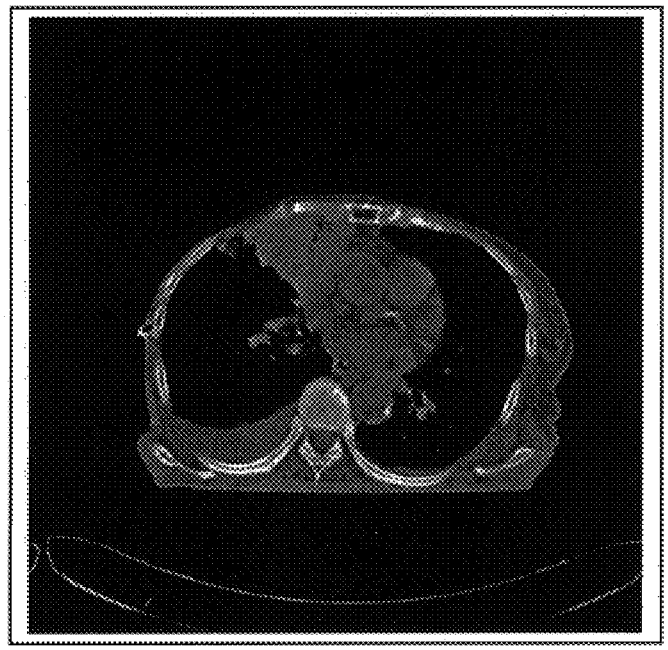
Figure 27  Corrected image for human patient using the CSS-SSOC method on the data sets of Figure 26.

METHOD FOR TRACING ORGAN MOTION AND REMOVING ARTIFACTS FOR COMPUTED TOMOGRAPHY IMAGING SYSTEMS

RELATIONSHIP TO OTHER APPLICATIONS

This is a continuation in part of U.S. application Ser. No. 09/334,640 in the name of Stergiopoulos et al. filed on Jun. 17, 1999 is now U.S. Pat. No. 6,236,705.

FIELD OF THE INVENTION

This invention relates generally to image reconstruction in computer tomography and more particularly relates to a software-based method for tracking organ motion and for motion correction.

BACKGROUND OF THE INVENTION

In computer tomography, 2-D or 3-D image reconstruction is performed using projection data acquired over a period of time in a scan comprised of a series of projections. Each projection is a snapshot of a patient's organs from a different angle, or perspective, and a scan typically includes hundreds of projections. Prior art methods used to reconstruct images from such data presume the patient and his organs are motionless during the entire scan such that a same fixed object is the subject of all acquired projections. Organ motion such as cardiac motion, blood flow, lung respiration or a patient's restlessness during an acquisition process produces artifacts that appear as a blurring effect in the reconstructed image. Such blurring effects substantially complicate diagnosis or may even lead to inaccurate diagnosis putting the patient's health at risk. Furthermore, repeating a scan in case of a complicated diagnosis due to blurring effects exposes the patient unnecessarily to radiation such as X-rays.

Speeding up data acquisition to reduce the blurring effects of organ motion is not possible with current x-ray tube technology. Therefore, signal processing algorithms accounting for organ motion have to be applied in the image reconstruction process.

Several techniques have been proposed to reduce the effects of organ motion. Srinivas, C. and Costa, M. H. M. in "Motion-compensated CT image reconstruction", Proceedings of the IEEE Ultrasonics Symposium, 1, pp. 849–853, 1994, teach motion compensation using a linear model assuming translation and rotation. In U.S. Pat. No. 5,323,007 issued Jun. 21, 1994, Wernick et al. disclose a method for motion compensation using two projections of an object taken from different locations at different time instances. Organ motion is then measured from known image elements and an image is then corrected by solving a set of linear equations. Other techniques model organ motion as a periodic sequence and take projections at a particular point of the motion cycle or to correct image data using motion trajectories obtained from Fourier harmonics as disclosed in U.S. Pat. No. 5,615,677 to Pelc et al. issued Apr. 1, 1997. However, organ motion is too complex for these methods to substantially reduce the blurring effects and makes the prior art methods useful only in a very limited number of cases. In "Tomographic Reconstruction Of Time Varying Object From Linear Time-Sequential Sampled Projections", Proceedings of the IEEE, 0-7803-1775-0/94, pp. 309–312, 1994, Chiu, Y. H. and Yau, S. F. teach a method for compensating for organ motion by iteratively suppressing motion effects from the projections. This method reduces assumed spectral characteristics of the motion artifacts. The method depends on knowledge of at least some properties of the organ motion and requires a substantial number of iterations to converge, thereby requiring a large amount of computing time. In U.S. Pat. No. 5,671,263 issued Sep. 23, 1997, Ching-Ming discloses another spectral method for motion compensation. A high frequency signal of the organ motion is obtained using a high pass filter. The high frequency signal is then subtracted from the projection signal to remove motion artifacts. Unfortunately, removing high frequency components from the projection signal removes small size spatial structures from the image, as well.

In U.S. Pat. No. 5,806,521 issued Sep. 15, 1998, Morimoto et al. disclose a method for motion compensation based on correlating overlapping converted image data in an ultrasound imaging apparatus. In successive image frames a majority of information results from a same geometry. Due to this redundant information the data of two successive image frames is highly correlated. Organ motion between the acquisition of two frames will result in a shift of the correlation peak of the two frames with respect to each other corresponding to the amount of relative motion. Unfortunately, correlation of the two successive image frames taken from different spatial locations results only in a minor reduction of motion artifacts and, furthermore, may lead to cancellation of image details.

It is an object of the invention to provide a method for tracking organ motion and removing motion artifacts, which overcomes the aforementioned problems and substantially reduces motion artifacts in images of a large variety of CT scans.

It is further an object of the invention to provide a software-based method for tracking organ motion and removing motion artifacts for implementation in existing CT systems without major hardware modification.

SUMMARY OF THE INVENTION

In accordance with the invention, there is provided, a method of tracking motion present during computer tomography scan data acquisition of an object, the method comprising the steps of:

receiving a sensor time series indicative of image data of the object from a CT scanner;

providing the sensor time series to a processor; and, using the processor, comparing image data of the object acquired from identical spatial locations at different times t and t+T to obtain information about the phase of the motion of the moving object and determining a sinogram indicative of the position of the object at the time instance each image is taken.

In accordance with the invention, there is provided, a method of motion correction in image data of computer tomography scans of an object comprising the steps of:

providing to a processor a sinogram indicative of the position of the object at the time instance each image is taken; and, using the processor, determining motion corrected image data from the sinogram using retrospective gating.

In accordance with another aspect of the invention, there is provided, a method of motion correction in image data of computer tomography scans of an object comprising the steps of:

providing to a processor a sinogram indicative of the position of the object at the time instance each image is taken;

using the processor:
defining a phase of interest of the sinogram;
isolating every subsequent time instance during the data acquisition period when the object is again at the pre-selected phase of its motion cycle;
selecting a number of projections at each of the time instances;
assembling the projections into a phase coherent sinogram; and,
reconstructing an image of the object at the phase of interest based on the phase coherent sinogram.

In accordance with the invention, there is further provided, an image data processing system for tracking motion present during computer tomography scan data acquisition of an object, the system comprising:
port for receiving a sensor time series indicative of image data of the object from a CT scanner; and,
a processor for performing the steps of:
comparing image data of the object acquired from identical spatial locations at different times t and t+T to obtain information about the phase of the motion of the moving object; and,
determining a sinogram indicative of the position of the object at the time instance each image is taken.

In accordance with yet another aspect of the invention, there is provided, a method of generating a computer tomography motion picture of a moving object comprising the steps of:
providing to a processor a sinogram indicative of the position of the object at the time instance each image is taken;
using the processor:
defining a number of phases of interest of the sinogram, wherein the phases of interest are equally spaced over a single motion cycle of the object;
isolating every subsequent time instance during the data acquisition period when the object is again at the pre-selected phases of its motion cycle;
selecting a number of projections at each of the time instances;
assembling the projections into phase coherent sinograms; and,
reconstructing an image of the object at each of the phases of interest based on the phase coherent sinograms.

BRIEF DESCRIPTION OF THE DRAWINGS

An exemplary embodiment of the invention will now be discussed in conjunction with the attached drawings in which:

FIGS. 12–12c illustrate the image sampling process using a conventional CT scanner;

FIG. 26 shows a conventional CT image; and

FIG. 27 shows the corresponding image to FIG. 26 but with motion correction using the SSOC and CSS methods according to the invention.

DESCRIPTION OF THE PREFERRED EMBODIMENTS

Figure 1:
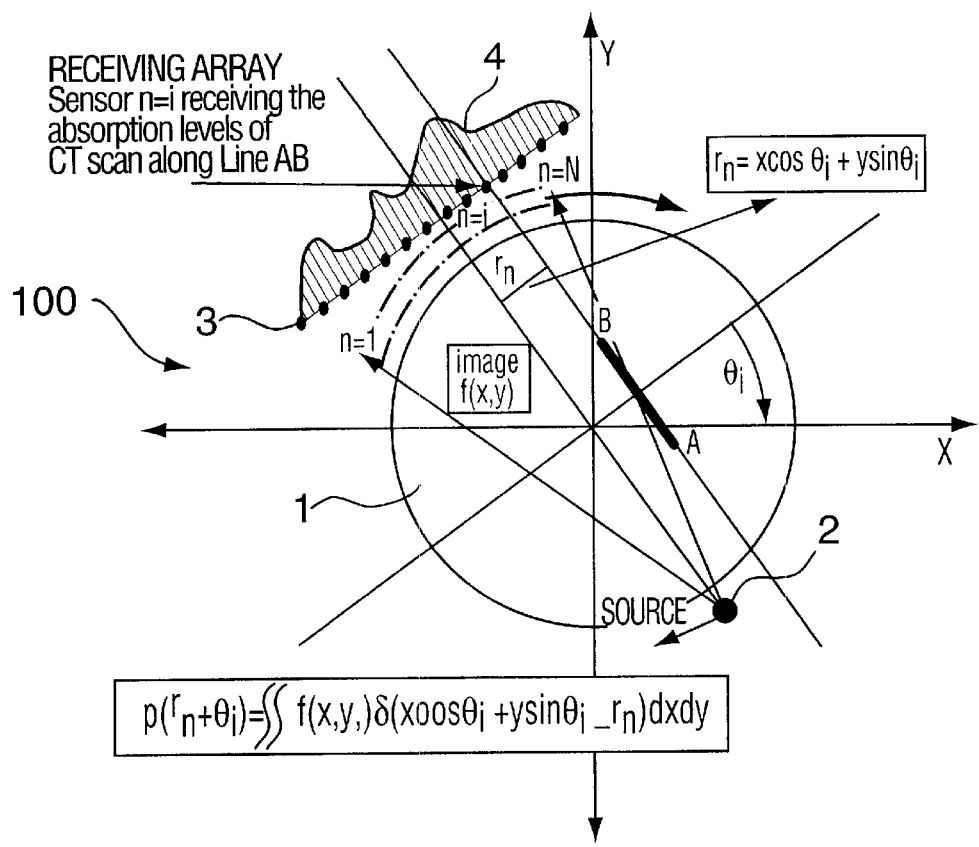
FIG. 1 is a schematic diagram of a data acquisition process for an X-ray CT scanner.

Referring to FIG. 1, a schematic view shows the basic principle of a representative embodiment of a known type of computer tomographical (CT) scanner 100. An object 1, shown in FIG. 1 in an x, y plane, is irradiated by an energy emitting source 2 such as an X-ray source. Alternatively, other sources such as ultra sound and MRI are used. The radiation emitted by the source 2 penetrates the object 1 along straight lines, for example line AB shown in FIG. 1.

While penetrating the object 1 the radiation is absorbed by matter of the object 1 typically in the form of tissue. Different types of matter absorb the radiation differently. A receiving sensor array 3 located opposite the source 2 detects the remaining radiation not absorbed by the matter of the object 1 along various straight lines originating from the source 2 and penetrating the object 1. Thus, the receiving sensor array 3 provides projection measurement data 4 of the object 1 comprising different absorption levels along the various straight lines. The source 2 and the receiving array 3 are rotated around the object 1 in angular step increments. After each increment the object 1 is irradiated and a projection image is taken.

The projection measurement data 4 provided by the receiving sensor array 3, $\{P_n(r_n, \theta_i),(n=1, \ldots, N)\}$, are defined as line integrals along the straight lines through the object 1 in the x, y plane, for example, line AB. Image $f(x,y)$ indicates the cross section of the object 1 in the x, y plane. The projection measurement data for parallel projection CT scanners are defined as follows:

$$P_n(r_n, \theta_i) = \int\int f(x,y)\delta\{x \cos \theta_i + y \sin \theta_i - r_n\}dxdy. \quad (1)$$

For fan beam CT scanners, the projection image data 4 include the following parameters of the coordinate system: $r_n = R \sin\sigma_n$, $\theta_i = \sigma_n + \beta_i$. The projection measurement data are, therefore, defined by:

$$g_n(\sigma_n, \beta_i) = P_n\{[r_n = R \sin\sigma_n],[\theta_i = \sigma_n + \beta_i]\}. \quad (2)$$

Organ motion such as cardiac motion, blood flow, lung respiration or a patient's restlessness during acquisition of the projection image data produces artifacts, which appear as a blurring effect in the reconstructed image. According to the invention adaptive and synthetic-aperture processing schemes are applied in order to remove motion artifacts. The adaptive and synthetic-aperture processing schemes are based on computing an appropriate phase correction factor to coherently synthesize spatial measurements. To apply these processing schemes for correcting motion artifacts in CT scans a comparison of spatially overlapping measurements is needed in order to obtain a phase correction factor. The phase correction factor provides data indicative of organ motion and is then used to compensate phase and/or amplitude fluctuations caused by the organ motion.

Figure 2:
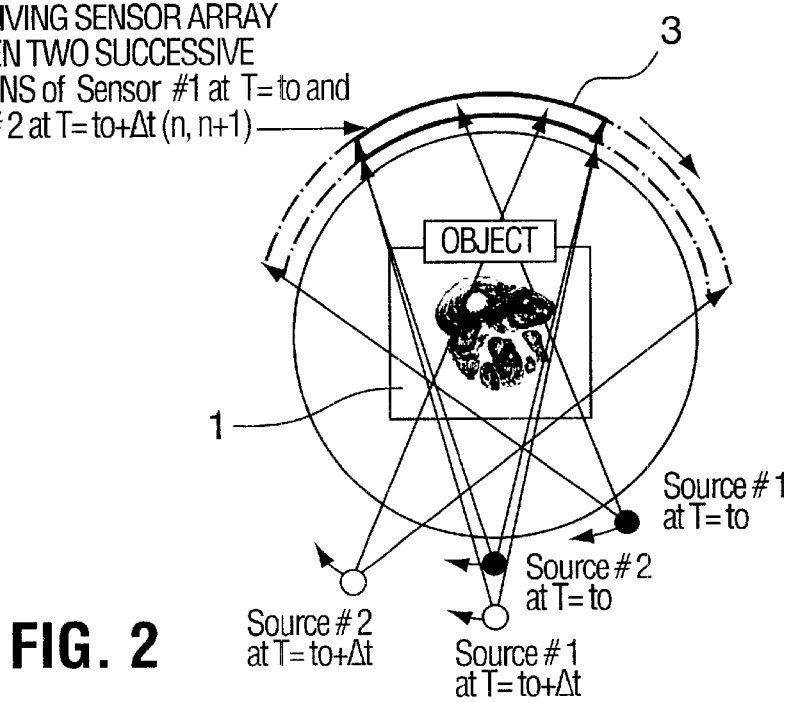
FIG. 2 is a schematic diagram of a data acquisition process according to the invention comprising two sources.

FIG. 2 illustrates an implementation of a spatial overlap correlator method for CT scans according to the invention. An object 1 is irradiated at time $t_0$ by two energy emitting sources—source #1 and source #2—at different spatial locations $s_0$ and $S_1$, indicated by dark dots. A receiving sensor array 3 provides projection measurement data of the object 1 based on the same principle as shown in FIG. 1. At time $(t_0+\Delta t)$ the two sources have been rotated about an angular step increment such that the sources are at spatial locations $S_1$, and $S_2$, indicated by lighter dots. As shown in FIG. 2, the object 1 is irradiated from location $s_1$ by source #2 at time to and by source #2 at time $(t_0+\Delta t)$. The process is repeated throughout a data acquisition period T and, therefore, provides two spatially identical sets of projection measurement data at any given spatial location and at two successive time instances, separated by $\Delta t$, wherein $\Delta t = T/M$ is the time interval between two successive firings of the X-ray sources. Correlation of two sets of spatially overlapping projection measurement data provides data indicative of organ motion during the time interval $\Delta t$. Supposed $$\{P_{n_{s1}}(r(t),\theta(t),t_0),(n_{s1}=q,q=1,\ldots,N)\}\&$$
$$\{P_{n_{s2}}(r(t),\theta(t),t_0+\Delta t),(n_{s2}=1,2,\ldots,N-q)\} \quad (3)$$

are (N-q) spatially overlapping projection image data received by the N-element sensor array 3 at the two successive time instances $t_0$ and $(t_0+\Delta t)$ as illustrated by the shaded area in FIG. 2. Based on equation (2), the time dependency of the projection image data for a fan-beam CT scanner is expressed by:

$$g_n(\sigma(t),\beta(t),t_0) = \int\int f(x,y,t)\delta\{x \cos[\sigma(t)+\beta(t)] + y \sin[\sigma(t)+\beta(t)] - R \sin \sigma(t)\}dxdy, \quad (4)$$

wherein $f(x,y,t)$ is the time varying cross section of the object 1 in the x, y plane. The amplitude difference between the two sets of projection measurement data of equation (3) is defined by:

$$\Delta p_{n_0}(r(t),\theta(t),t_0+\Delta t) = p_{n_{s2}}(r(t),\theta(t),t_0+\Delta t) - p_{n_{s1}}(r(t),\theta(t),t_0), \text{ for } (n_0=1, 2,\ldots,N-q) \quad (5)$$

For fan-beam CT scanners the difference is defined by:

$$\Delta g_{n_0}(\sigma(t),\beta(t),t_0+\Delta t) = g_{n_{s2}}(\sigma(t),\beta(t),t_0+\Delta t) - g_{n_{s1}}(\sigma(t),\beta(t),t_0), \text{ for } (n_0=1, 2,\ldots,N-q) \quad (6)$$

Introducing the spatial overlap concept of equation (3), which assumes that $$\{\beta_{s1}(t_0+\Delta t) = \beta_{s2}(t_0)\}, \{\sigma_{s1}(t_0+\Delta t) = \sigma_{s2}(t_0)\},$$

together with equation (4) into equation (6) provides the amplitude difference as follows:

$$\Delta g_{n_0}(\sigma(t), \beta(t), t_0 + \Delta t) = \qquad (7)$$
$$\int\int [f(x, y, t_0 + \Delta t) - f(x, y, t_0)]\delta\begin{Bmatrix} x\cos[\sigma_{s2}(t_0) + \beta_{s2}(t_0)] + \\ y\sin[\sigma_{s2}(t_0) + \beta_{s2}(t_0)] - \\ R\sin\sigma_{s2}(t_0) \end{Bmatrix} dx\,dy,$$

wherein $[f(x,y,t_0+\Delta t) - f(x,y,t_0)]$ indicates the tomography difference of the time varying cross section of the object 1 in the x, y plane between the time instances $t_0$ and $(t_0+\Delta t)$.

The projection image data acquired using the spatial overlap correlator method as shown in FIG. 2 and defined by equations (6) and (7) may be provided to an image reconstruction algorithm. The image reconstruction algorithm will reconstruct time dependent image changes $[f(x,y,t_0+T)-f(x,y,t_0)]$ taking place during the time period T of the CT scan data acquisition process. In case there is no motion present during the data acquisition process the spatial overlapping projection images are identical and the result of equation (7) is zero. That is, the image reconstruction algorithm of equation (7) tracks only moving components of the projection measurements, whereas stationary components do not appear in reconstructed images. Images containing only moving components may be of diagnostic value in some special applications, for example, displaying heart functions, but in general it is required to reconstruct images containing also the stationary components of the projection measurement data.

Figure 3A:
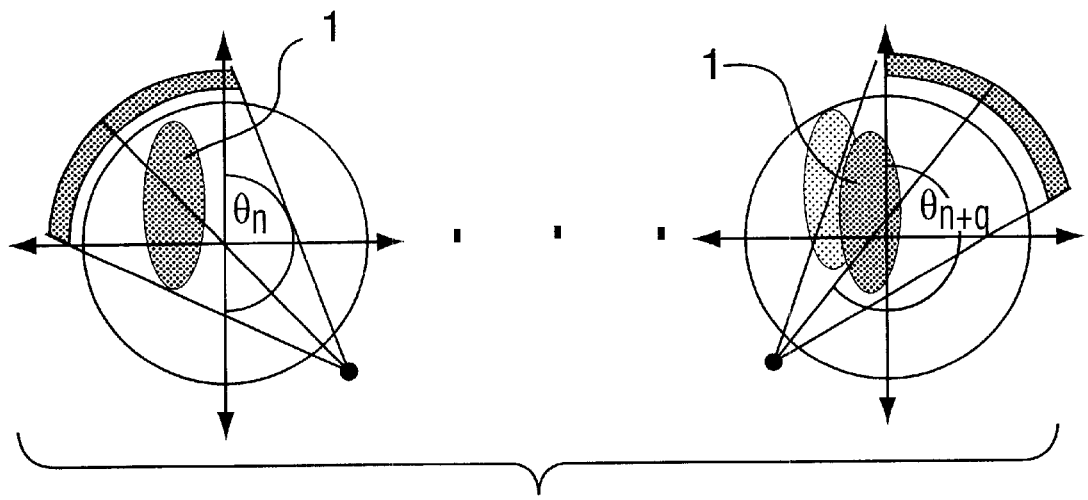
FIGS. 3a and 3b are diagrams used in explanation of a spatial overlap correlator method according to the invention.
Figure 3B:
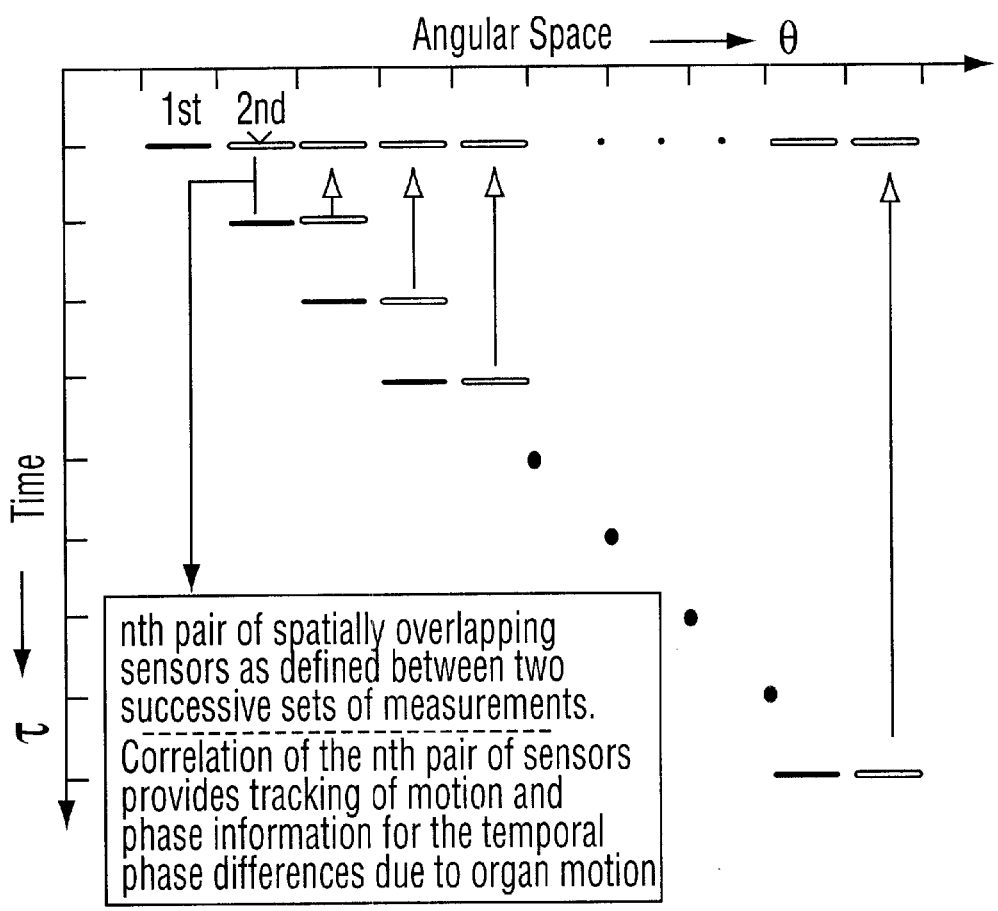

FIGS. 3a and 3b illustrate the data acquisition process using the spatial overlap correlator method shown in FIG. 2 and defined by equations (6) and (7) in a space-time diagram. In FIG. 3b, the vertical axis is the time axis displaying the different time instances separated by the time difference $\Delta t$. The horizontal axis shows the angular position of source #1 and source #2. Image reconstruction algorithms according to the prior art assume stationarity during the data acquisition process or all projection images, indicated by line segments parallel to the horizontal axis, being taken at a same time instance, that is, all line segments are aligned in one line parallel to the horizontal axis. However, during the data acquisition period T the object 1 (FIG. 3a) may vary with time due to organ motion. The projection measurement data acquired using the spatial overlap correlator method are represented by line segments along the diagonal, two line segments for each time instance wherein $1^{st}$ indicates source #1 and $2^{nd}$ indicates source #2. Spatially overlapping projection measurements are indicated by line segments taken at two successive time instances and overlapping in angular space.

An obvious method to correct for organ motion during the image reconstruction process is to remove temporal amplitude and phase differences due to organ motion between the spatially overlapping projection images. Ideally, this correction method corrects the projection images with respect to the first acquired projection image. This is equivalent to moving all projection images into a same time instance, that is, all line segments along the diagonal being moved into one line parallel to the horizontal axis as shown in FIG. 3b. Unfortunately, this method does not produce satisfactory results because of the very large number M of projection measurements acquired in CT scans. As a result, errors generated during correction of each projection measurement propagate to the correction of the following projection measurement. The error propagation during image reconstruction leads to a significant error accumulation covering all useful information.

A method to remove motion artifacts in image reconstruction of CT scans according to the invention uses an adaptive processing scheme, in particular, an adaptive interferer canceller. Details concerning the adaptive processing scheme are disclosed by the inventor in "Limitations on towed-array gain imposed by a nonisotropic ocean", published in Journal of Acoustic Society of America, 90(6), 3131–3172, 1991, and in "Implementation of Adaptive and Synthetic-Aperture Processing Schemes in Integrated Active-Passive Sonar Systems", published in Proceedings of the IEEE, 86(2), 358–396, February 1998. The adaptive interferer canceller is useful when an interferer is accurately measured. Using tracked organ motion as interferer, the adaptive interferer canceller is an ideal tool for removing motion artifacts from reconstructed images of CT scans. Sensor time series, that is, a series of measurements of one sensor at different time instances, are treated as an input signal of the adaptive interferer canceller algorithm, wherein the input signal comprises noise due to organ motion. The organ motion tracked by the spatial overlap correlator is introduced into the adaptive interferer canceller algorithm as interference noise. The adaptive interferer canceller algorithm then removes the interference noise from the input signal.

Figure 4A:
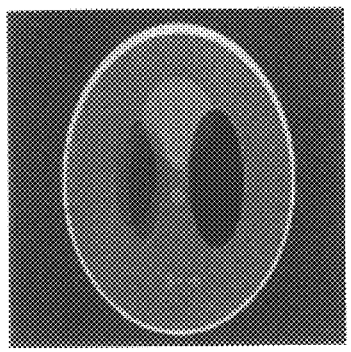
FIGS. 4a–4f are diagrams which illustrate removal of motion artifacts using an adaptive processing method according to the invention.
Figure 4B:
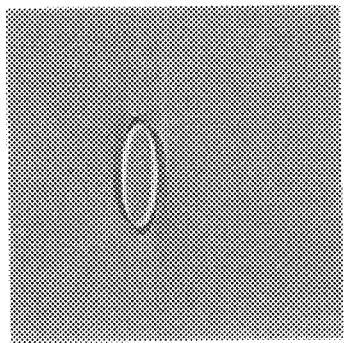
Figure 4C:
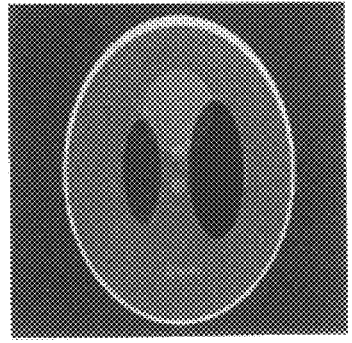

FIGS. 4a, 4b and 4c show a comparison of reconstructed images of the Shepp-Logan phantom using three different methods. Detailed information about the Shepp-Logan phantom is taught by KaK, A. C., in "Image Reconstruction from Projections", chap. 4 in Digital Image Processing Techniques, Academic Press, New York, 1984. Projection image data of the Shepp-Logan test image have been processed using a prior art method, the reconstruction method for the spatial overlap correlator expressed by equations (6) and (7), and the spatial overlap correlator method combined with the adaptive intereferer canceller algorithm. The prior art method comprises a filtered back-projection method including a Ram-Lak filter cascaded with a Parzen window as taught by KaK, A. C. in the publication mentioned above. Geometry and parameters used in the simulations were equivalent to Elcint's CT Twin RTS medical tomography system.

The upper right image in FIG. 4c shows the reconstruction of the Shepp-Logan phantom using the spatial overlap correlator method combined with the adaptive intereferer canceller algorithm according to the invention. The projection measurement data for the Shepp-Logan phantom included simulated motion of the left interior ellipse taking place during the data acquisition period of the CT scan. As is evident, the method for removing motion artifacts according to the invention is very effective. The image shows clearly the details of the Shepp-Logan phantom having sharp contours including the moving ellipse.

In contrast, the upper left image of FIG. 4a, reconstructed using the prior art method, is blurred due to the motion of the left interior ellipse. All contours within the image are blurred and the different components cannot be distinguished. Such an image makes a reliable diagnosis very difficult if not impossible.

The upper middle image of FIG. 4b shows the result of the reconstruction process according to the invention expressed by equations (6) and (7). The reconstructed image shows only the moving left interior ellipse. This result is sometimes of diagnostic value in some special applications, for example, displaying heart functions. Furthermore, it provides valuable information for motion artefact removal.

Figure 4D:
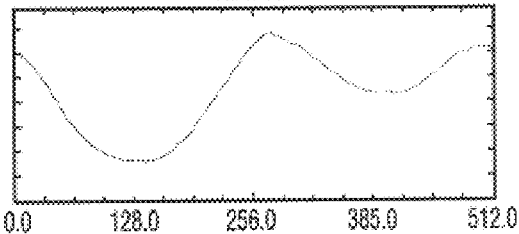
Figure 4E:
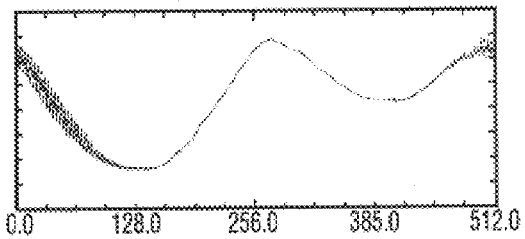
Figure 4F:
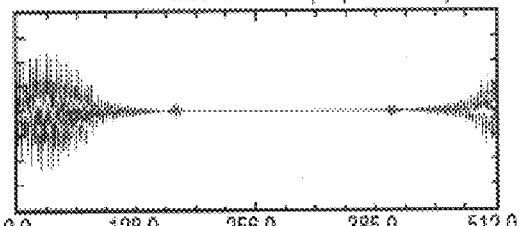
Figure 4G:
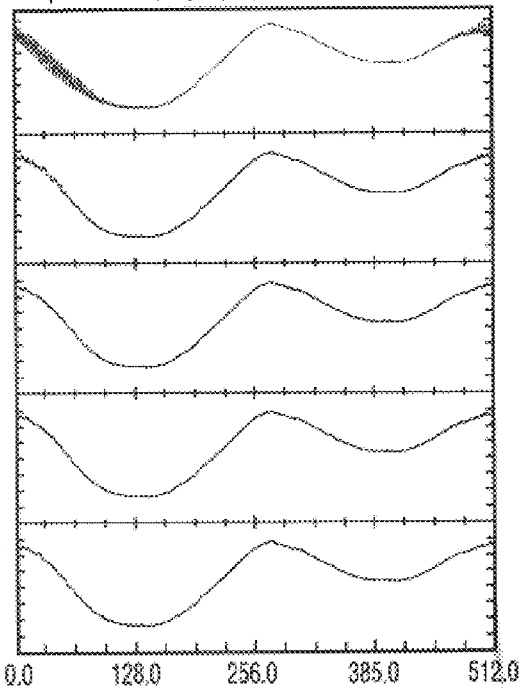

FIGS. 4d, 4d and 4f show the sensor time series of a typical sensor during the data acquisition process of a CT scanner for a full rotation of 360°. The top right curve of FIG. 4d is a sensor time series for the simulated phantom without motion. The center right curve of FIG. 4e shows the same sensor time series with motion of the left interior ellipse of the phantom. As is evident, the motion of the left interior ellipse introduces a high frequency disturbance into the sensor time series. The lower right curve of FIG. 3f shows the sensor time series provided by the spatial overlap correlator method containing only the high frequency disturbance associated with the organ motion. FIG. 4g shows the result of the adaptive processing method according to the invention. The upper curve in the panel shows the sensor time series with motion of the left interior ellipse of the phantom. The curves below are sensor time series obtained with the adaptive processing method according to the invention. A substantial amount of the high frequency disturbances due to organ motion has been removed, thus providing evidence of the effectiveness of the method.

Figure 5A:
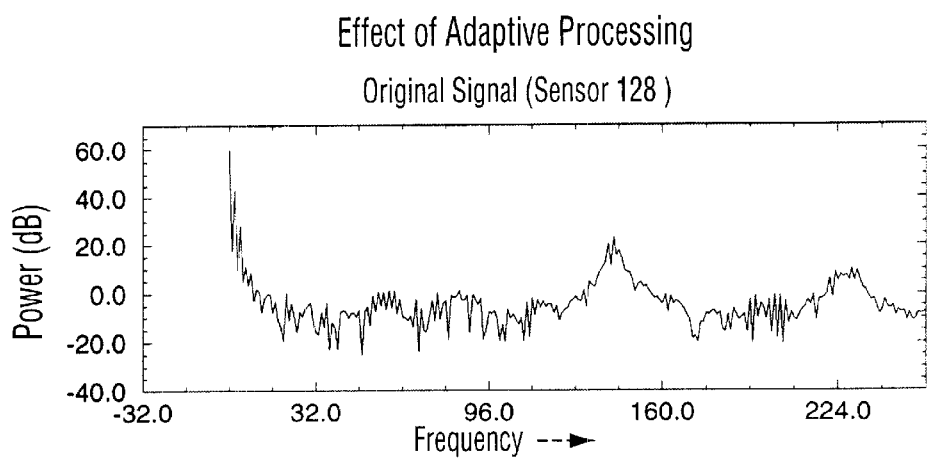
FIGS. 5a–5c are curves which illustrate a spectrum for various types of sensor time series.
Figure 5B:
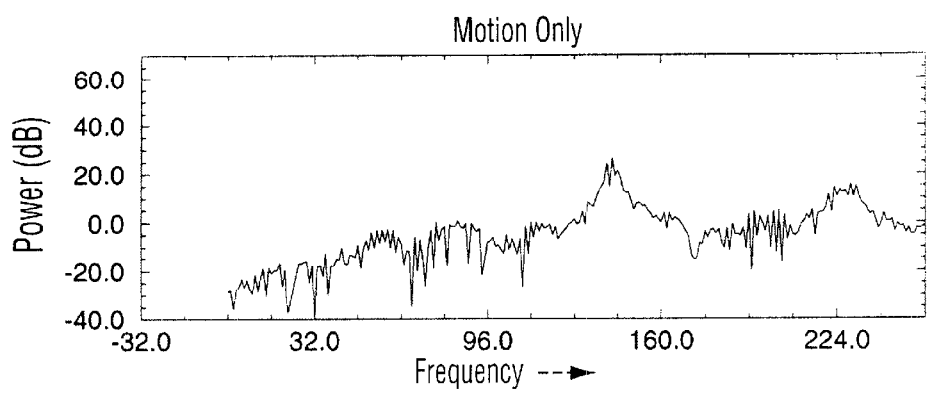
Figure 5C:
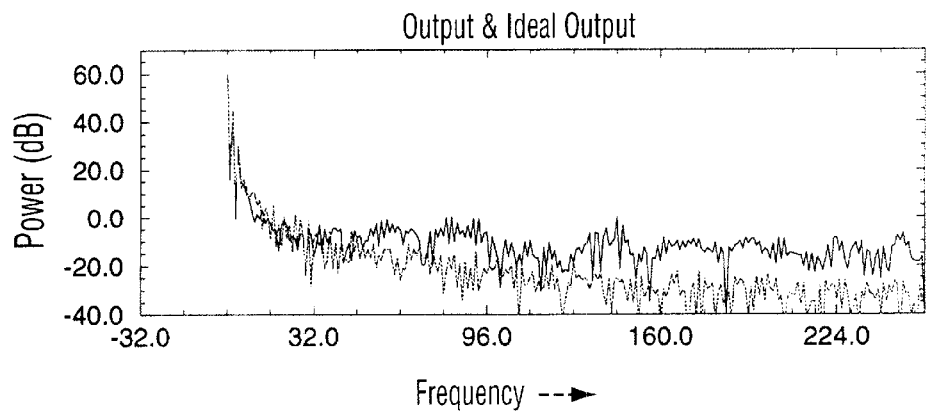

In order to obtain a quantitative measure of the effectiveness of the adaptive processing method according to the invention the spatial spectrum of the various types of sensor time series has been investigated. The upper curve of FIG. 5a shows the spatial spectrum of the sensor time series with motion of the left interior ellipse present. The center curve of FIG. 5b shows the spatial spectrum of the sensor time series after applying the spatial overlap correlator method. This curve corresponds to the lower curve of FIG. 4f. The lower diagram of FIG. 5c shows a comparison of the spatial spectrum of the sensor time series resulting from the adaptive processing method, indicated by the solid line, with the spatial spectrum of the sensor time series without motion of the left interior ellipse, indicated by the dashed line. It is apparent from this comparison that the adaptive processing method according to the invention suppresses the high frequency disturbances due to organ motion by approximately 40 dB. Comparison of these two curves also shows that this method does not remove small size spatial structures of the reconstructed image, that is, the peak and valley pattern of the spatial spectrum is not substantially altered by the adaptive processing method. Using a low pass filter suppresses the high frequency disturbances due to organ motion of the sensor time series; unfortunately, the low pass filter also suppresses high frequency components due to small size spatial structures in the tomography images as well.

Figure 6A:
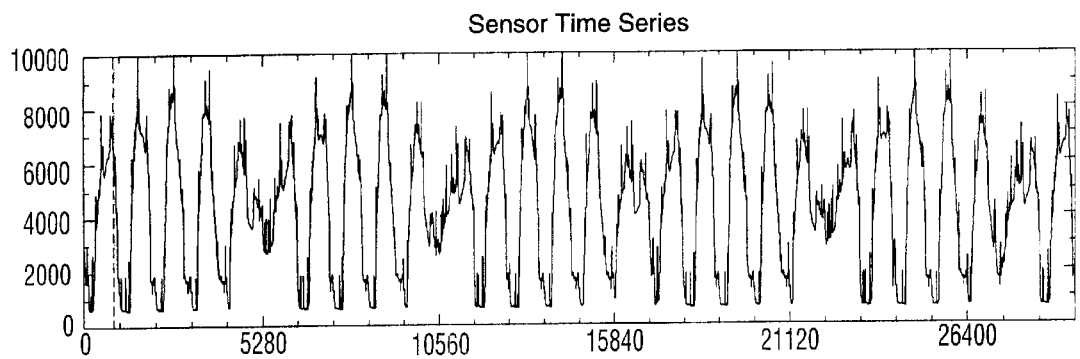
FIGS. 6a–6d illustrate processed sensor time series using a method according to the invention.
Figure 6B:
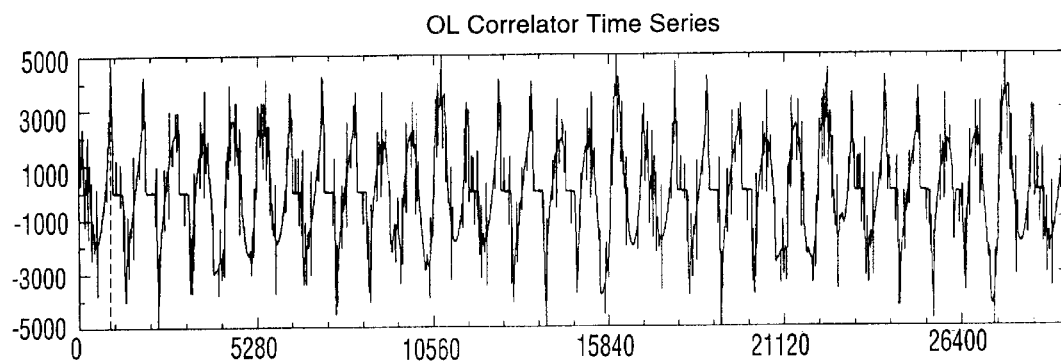
Figure 6C:
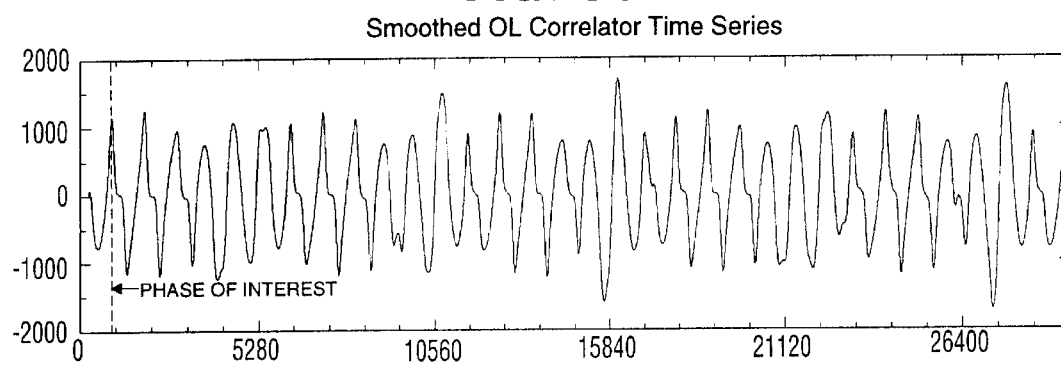
Figure 6D:
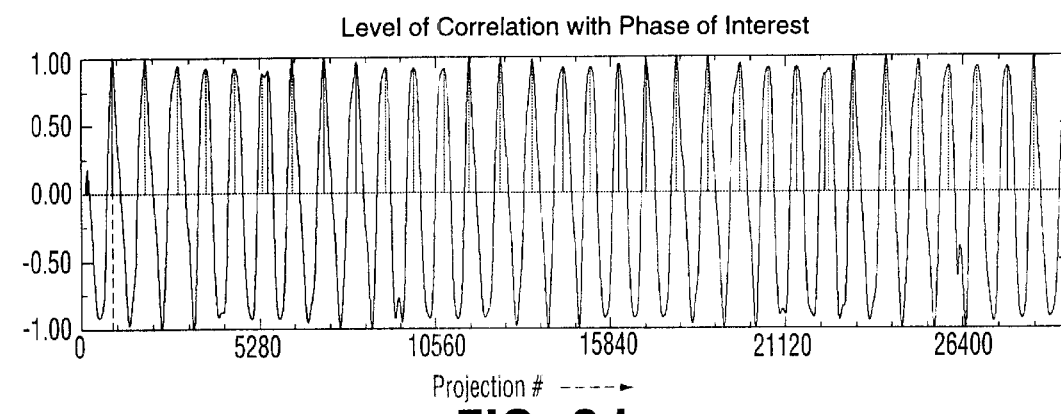

In another method according to the invention information obtained using the spatial overlap correlator is directly used to identify various phases of organ motion present during a CT - scan data acquisition period. A CT - scan data acquisition period typically lasts between 0.5 and 1.25 seconds. Evaluation of sensor time series obtained from the spatial overlap correlator provides information about amplitude and direction of the motion of an organ at any given time instance. Referring to FIGS. 6a–6d,the upper diagram of FIG. 6a shows a sensor time series for a typical X-ray CT - scanner. Periodicity of the organ motion such as a heartbeat is not evident from this curve. The second diagram from top, FIG. 6b, shows the sensor time series obtained using the spatial overlap correlator method. In order to remove high frequency disturbances introduced, for example, through background noise the sensor time series obtained using the spatial overlap correlator method has been smoothed as shown in the third diagram from top. Smoothing of measurement data is well known in the art and can be performed in time domain using smoothing filters, for example, Savitzky - Golay smoothing filters. As is evident, the curve shown in the third diagram, FIG. 6c, displays a periodic waveform. Different phases of the periodic waveform correspond directly to the various phases of the organ motion. A phase of interest corresponding to a specific phase of the organ motion has then to be selected. In the diagrams of FIGS. 6a–6d, the phase of interest is indicated by the dashed line. Autocorrelating the sensor time series shown in the third diagram with respect to the phase of interest reveals a repetition of the phase of interest in the remaining sensor time series. The autocorrelated sensor time series is shown in the fourth diagram from top, FIG. 6d. Time instances of the sensor time series with the organ being at a same point of its motion cycle - the phase of interest - are indicated by a level of correlation approaching one.

Figure 7:
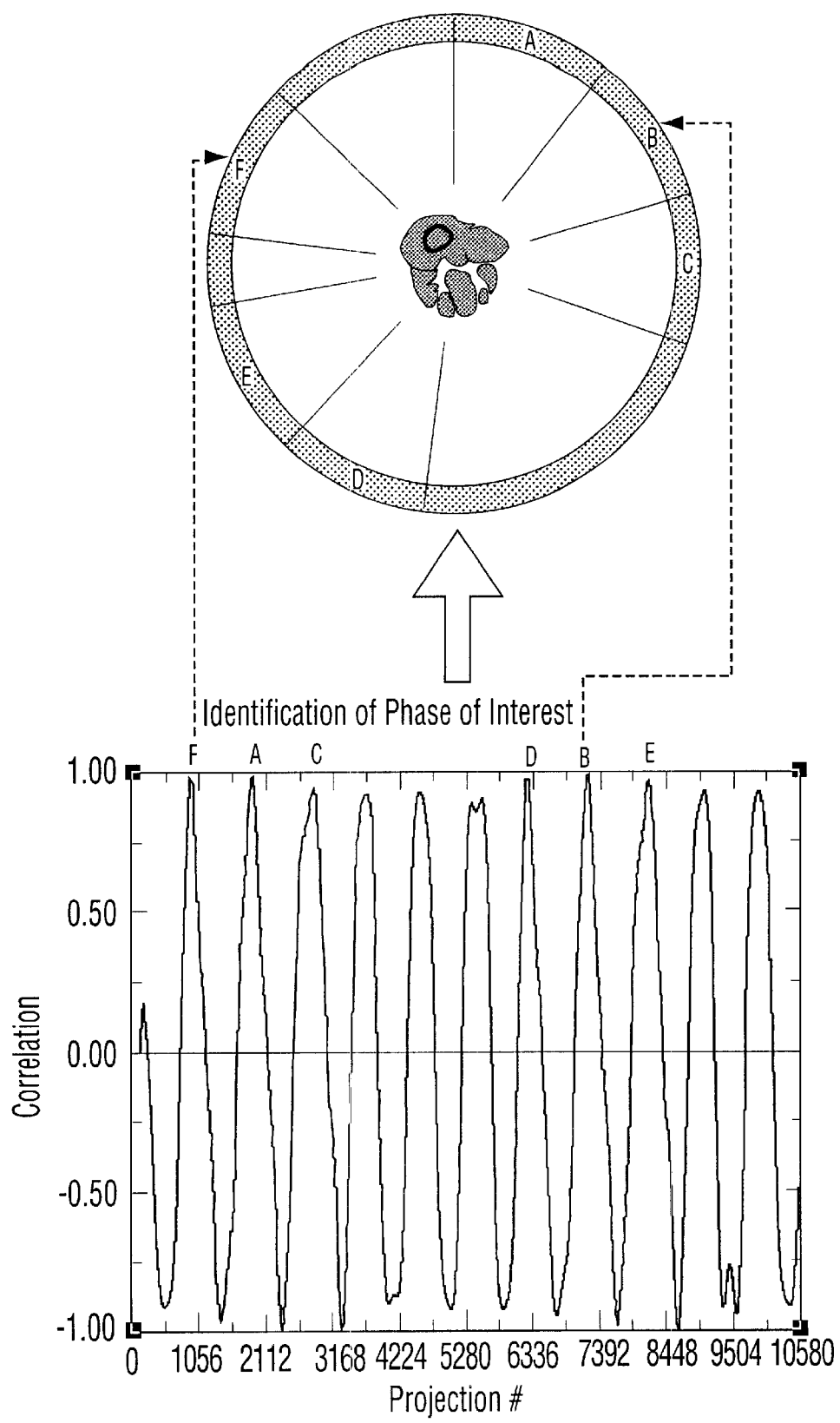
FIG. 7 illustrates creation of a sinogram according to the invention.

In order to create a sinogram for a single image of the organ at a desired point of its motion cycle segments of the sensor time series as shown in the third diagram from top have to be selected. For this purpose segments of the sensor time series with the organ motion being at the phase of interest have to be selected. The selection criterion for these segments is the level of correlation approaching one in the autocorrelation curve as shown in the fourth diagram from the top. FIG. 7 illustrates the autocorrelated sensor time series in relation to angular locations where projection image data of the sensor time series have been acquired relative to an object 1. The angular locations are determined by physical locations of a source and sensors (not shown in the figure) with respect to the object 1. As shown in FIG. 7, segments corresponding to projection image data taken in sectors B and F have a level of correlation approaching one, that is, the object 1 has been at a same phase of its motion cycle during acquisition of the projection image data in these sectors. Therefore, constructing a sinogram using only segments of the sensor time series having a correlation level approaching one is equivalent to freezing the motion of the object 1 to the selected phase of interest. Missing segments of the sensor time series are replaced using interpolation. Furthermore, number and size of missing sectors is reduced by increasing the number of sensors and/or acquiring sensor time series for more than one full rotation of the CT-scanner. Once a sinogram for a single phase of interest is completed an image of the object 1 is obtained using conventional image reconstruction methods. The resulting image is substantially free of motion artifacts equivalent to an image obtained from a stationary object. Of course, this method may be repeated for different phases of interest in order to obtain various images of the object 1 at different phases of its motion cycle. This method according to the invention is very helpful, for example, for the investigation of heart functions. Furthermore, this method allows to create a motion picture comprising a plurality of images following an entire motion cycle.

Figure 8A:
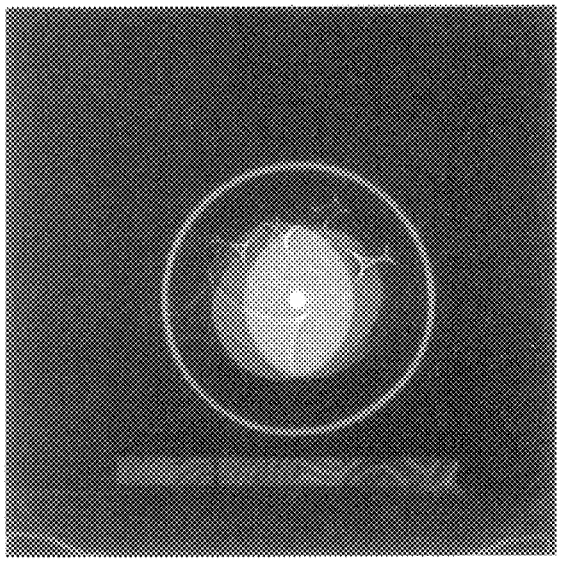
FIGS. 8a–8d are images which show results of motion artefact removal using the method according to the invention.
Figure 8B:
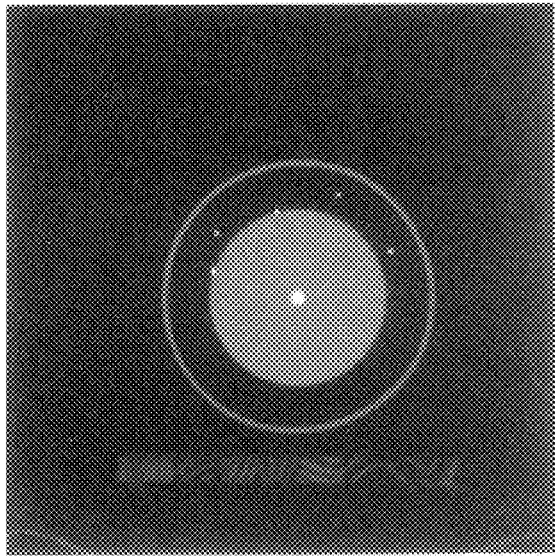
Figure 8C:
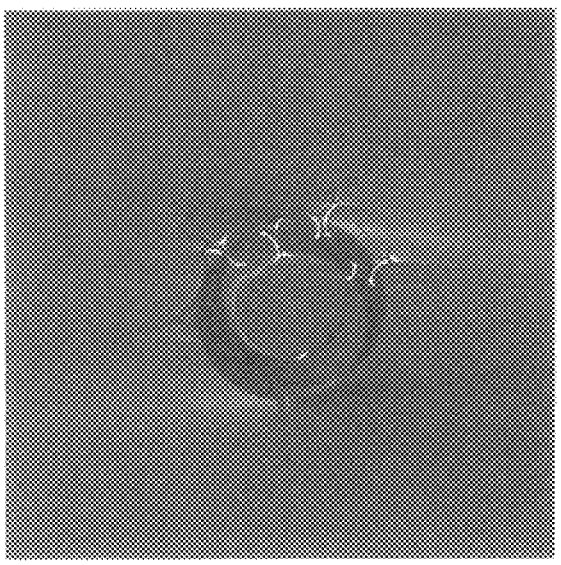
Figure 8D:
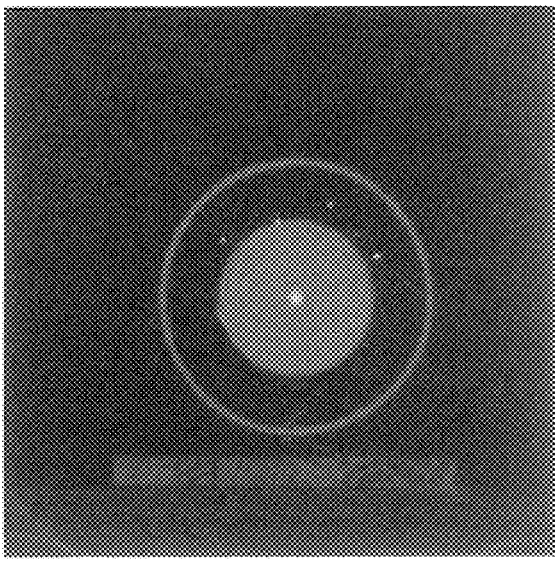

FIGS. 8a–8d show a comparison of images obtained using the method according to the invention with images obtained using a prior art method. The top left image, FIG. 8a, was obtained using an X - ray CT - scan system, according to the prior art, scanning a moving object. Comparison with the top right image, FIG. 8b, taken with the same system of the object being stationary illustrates severe distortion of the image by motion artifacts. As is obvious, the motion artifacts render the top left image, FIG. 8a, useless for any diagnosis. The bottom right image, FIG. 8d, is an X - ray CT - scan of the moving object using the method according to the invention to correct for motion artifacts. This corrected image is substantially identical to the top right image, FIG. 8a, of the stationary object. Using the method according to the invention to correct for motion artifacts improves significantly the functionality of CT systems. For example, current CT systems are not capable to detect calcifications - visible as white dots - in a heart's blood vessels as illustrated in the top left image, FIG. 8a. The calcifications appear as blurred lines and, therefore, it is impossible to make a diagnosis based on such an image. With an increasing number of patients having heart diseases the method according to the invention provides a new diagnostic tool that can save numerous lives. Of course, application of this method is not restricted to the investigation of heart function but allow use of CT scan in various application where the investigated object experiences some kind of motion.

Figure 9:
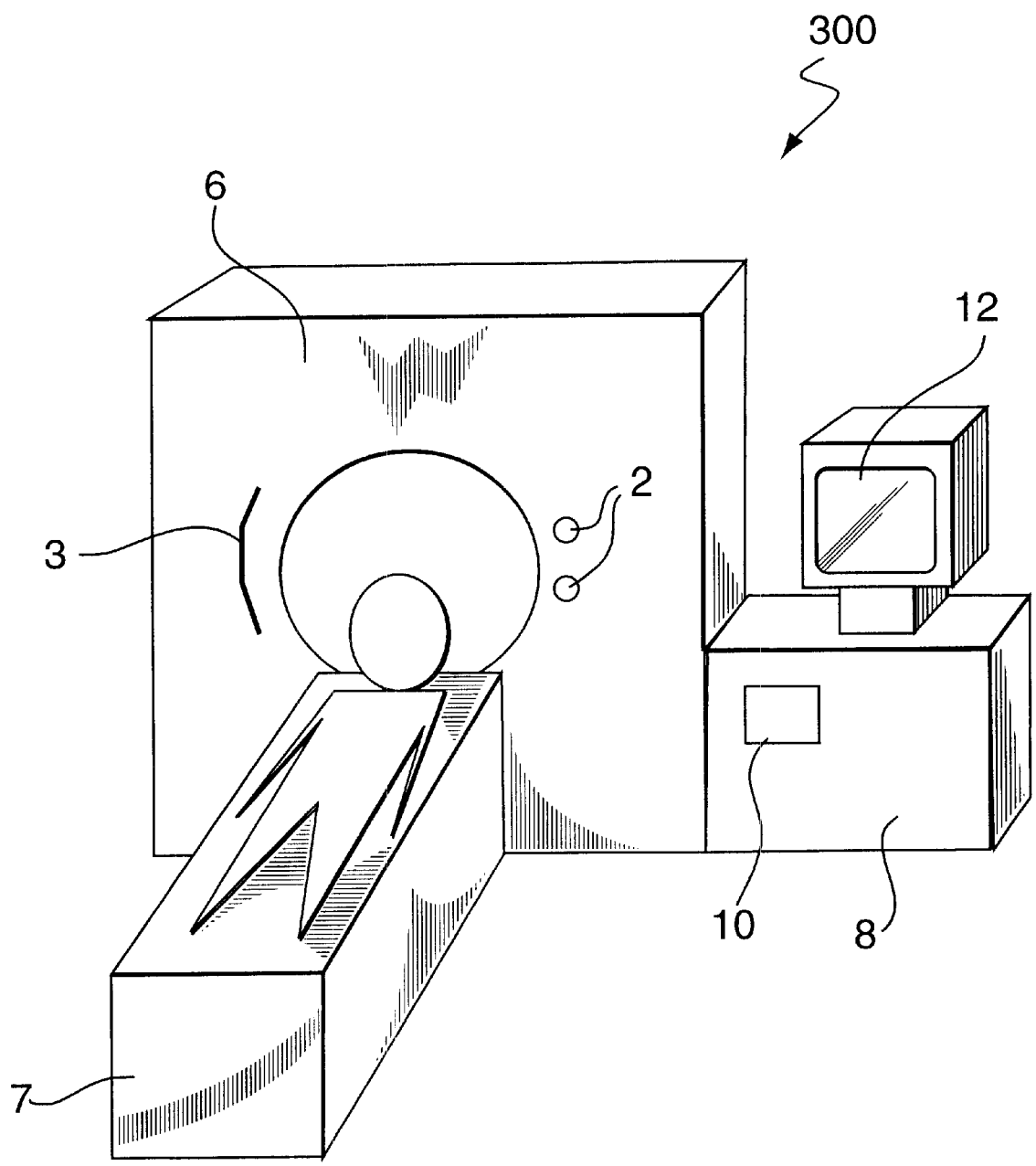
FIG. 9 illustrates a CT system according to the invention comprising two X-ray sources.

FIG. 9 shows a CT scanner 300 comprising a scanner unit 6, an object moving unit 7 and a processing unit 8. The scanner unit comprises two X-ray sources 2 and a receiving sensor array 3 rotatable 360° around an opening surrounding an object 1. Acquired data are being processed in the processing unit 8 comprising at least a processor 10 and reconstructed CT scan images are then displayed using display 12. An essential requirement of the spatial overlap correlator method is the implementation of the two X-ray sources 2 separated by an angular spacing equal to the sensor spacing of the receiving sensor array 3. However, state of the art X-ray sources are too big in size for implementation in a CT scanner with two sources.

Fortunately, the spatial overlap correlator method allows implementation in CT systems comprising flying focal point functionality such as Siemens CT systems or Elscint's CT Twin RTS system. The flying focal point functionality generates a second source 2 by deviating an electron beam by a magnetic field, which is defined as a new active emission of the source at an angle $\Delta\theta$ and time difference $\Delta t$ with respect to a previous source position. Typical values for $\Delta t$ are 1 ms providing spatial samples at ½ of the sensor spacing of the receiving sensor array 3. Therefore, the flying focal point functionality doubles a spatial sampling frequency of CT fan beam scanner without flying focal point. The spatial overlap correlator method according to the invention uses the flying focal point as a second source. The implementation of this method in CT systems with flying focal point functionality requires the second source being activated 1 ms after a previous X-ray emission and at a location of ⅛ sensor spacing to the location of the previous X-ray emission. The sensor time series associated with each one of the flying focal point X-ray source emissions have to be distinguished as defined by equation (6). Then, the sensor time series without any kind of pre-processing or image reconstruction are provided at the input of the proposed processing scheme.

Figure 10:
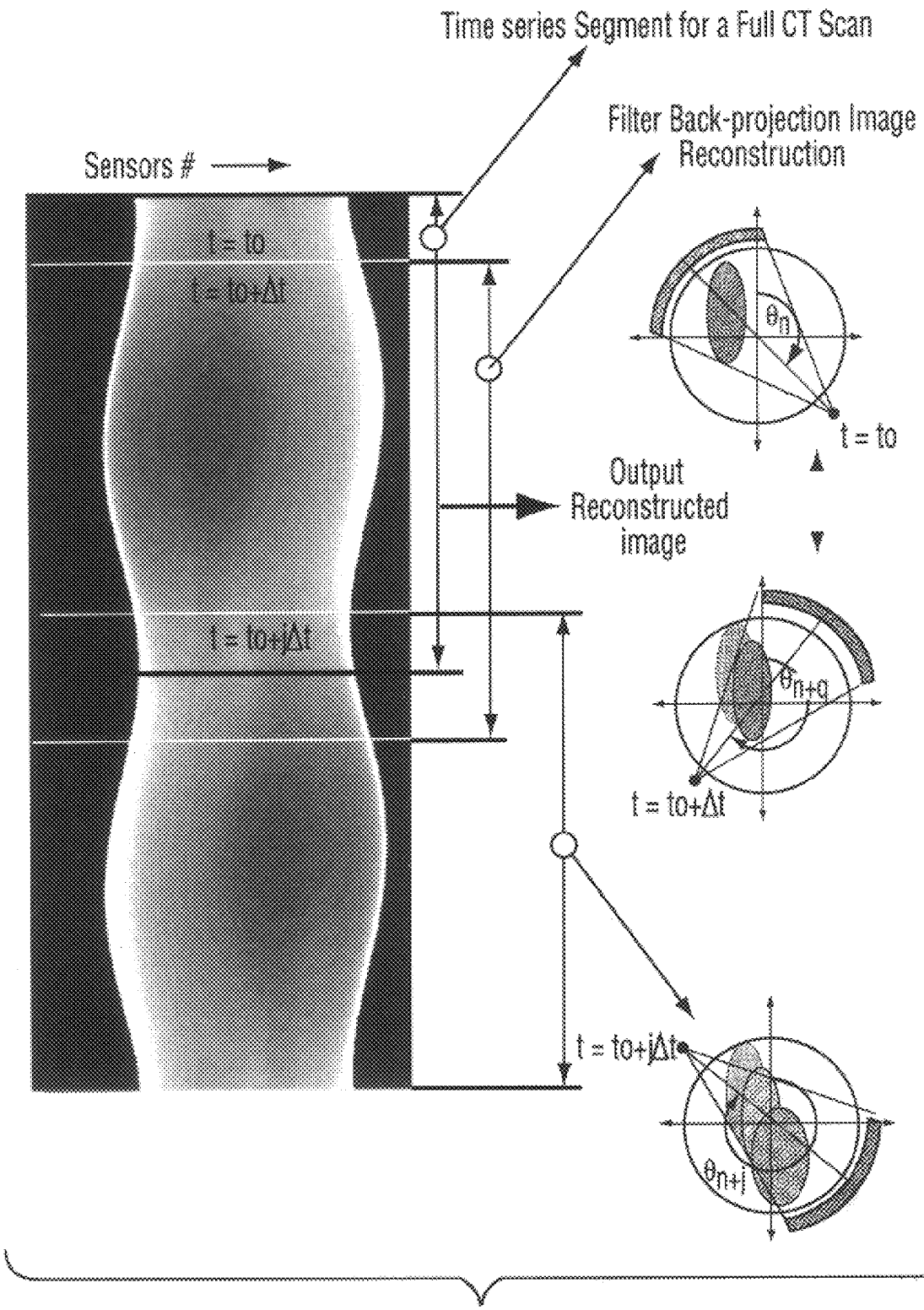
FIG. 10 is a schematic diagram of a method for generating motion pictures according to the invention.

Unfortunately, only the latest CT systems of Siemens and Elcint provide flying focal point functionality. Therefore, the implementation of the spatial overlap correlator method is presently restricted to implementation on only a small number of CT systems. Another method for tracking organ motion according to the invention does not require two sources as the spatial overlap correlator method. The left image of FIG. 10 illustrates measurements of all sensors of a receiving sensor array at different time instances. The measurements are displayed as a function of a plane defined by sensor number along the horizontal axis and time forming the vertical axis. Measurements of the receiving sensor array at a time instance comprise one line within the left image. The images at the right of FIG. 7 indicate different locations of a CT scanner comprising s source and a receiving sensor array with respect to an object for different time instances, as well as different locations of the moving object.

A time series segment-sinogram-associated with a full rotation of the CT scanner is defined as: $Z_n(j\Delta t), (n=1, 2, \ldots, N \& j=1, 2, \ldots, M)$, wherein N is the number of sensors of the receiving array of the CT system and M is the number of projections during one full rotation of the CT scanner. The above time series are processed using a filter back-projection algorithm to provide a reconstructed image of the object's cross section $f(x,y)$ in the x, y plane associated with the CT measurements. The next time series segment, $\Delta t$ seconds later, is defined as: $Z_n(j\Delta t), (n=1,2, \ldots, N \& j=2, \ldots, M+1)$. After processing using the filter back-projection algorithm it provides a reconstructed image of the object's cross section $f(x,y,\Delta t)$ comprising differences due to motion of the object and the CT scanner during the time interval $\Delta t$. For the second image to coincide with the first one rotation and alignment is required. Because the filter back-projection algorithm is a linear operator, the difference between the two images $\{f(x,y,\Delta t) - f(x,y)\}$ corresponds to the amplitude difference of the associated time series defined above. Therefore, a time series difference corresponding to the difference between the two images is defined by:

$$\Delta Z_n(j\Delta t) = \{Z_n[(M+j)\Delta t] - Z_n(j\Delta t)\}, (n=1, 2, \ldots, N \& j=1, 2, \ldots, M), \quad (8)$$

when appropriate image rotation is taken into account. Processing the time series difference $\Delta Z_n(j\Delta t)$ using the filter back-projection algorithm results in a reconstructed image tracking organ motion during the time interval $M\Delta t$ of the CT data acquisition. This information may then be used to remove motion artifacts using the adaptive processing method according to the invention. However, the effectiveness of the adaptive processing method combined with this method for tracking organ motion is reduced compared to the combination of the adaptive processing method with the spatial overlap correlator method. The reduction of effectiveness is caused by two fundamental differences between the two methods for tracking organ motion. Firstly, the second method tracks organ motion between two time instances separated by an initial time interval of $M\Delta t$. Secondly, the initial phase of the organ motion is out of phase with respect to the starting point of the CT data acquisition process. Therefore, the interference noise due to organ motion $\Delta Z_n(j\Delta t), (n=1, 2, \ldots, N \& j=1, 2, \ldots, M)$ is out of phase with respect to the noisy input signal $Z_n(j\Delta t)$, $(n=1, 2, \ldots, N \& j=2, \ldots, M+1)$.

In another embodiment of the second method for tracking organ motion according to the invention the processed time series differences $\Delta Z_n(j\Delta t)$ are used to produce a motion picture tracking organ motion observed during a long interval. For example, a CT scan over 30 seconds produces a set (of 300 images separated by time intervals of 0.1 seconds. Continuous viewing of the 300 images indicates periodic or aperiodic organ motion. Such a motion picture is a very helpful diagnostic tool for observing, for example, heart functions. Generation of the motion picture is based on the data acquisition process illustrated in FIG. 10. In this case the time interval $\Delta t$ is 0.1 seconds. Alternatively, motion information obtained by using the spatial overlap correlator method is used to generate a motion picture.

Figure 11:
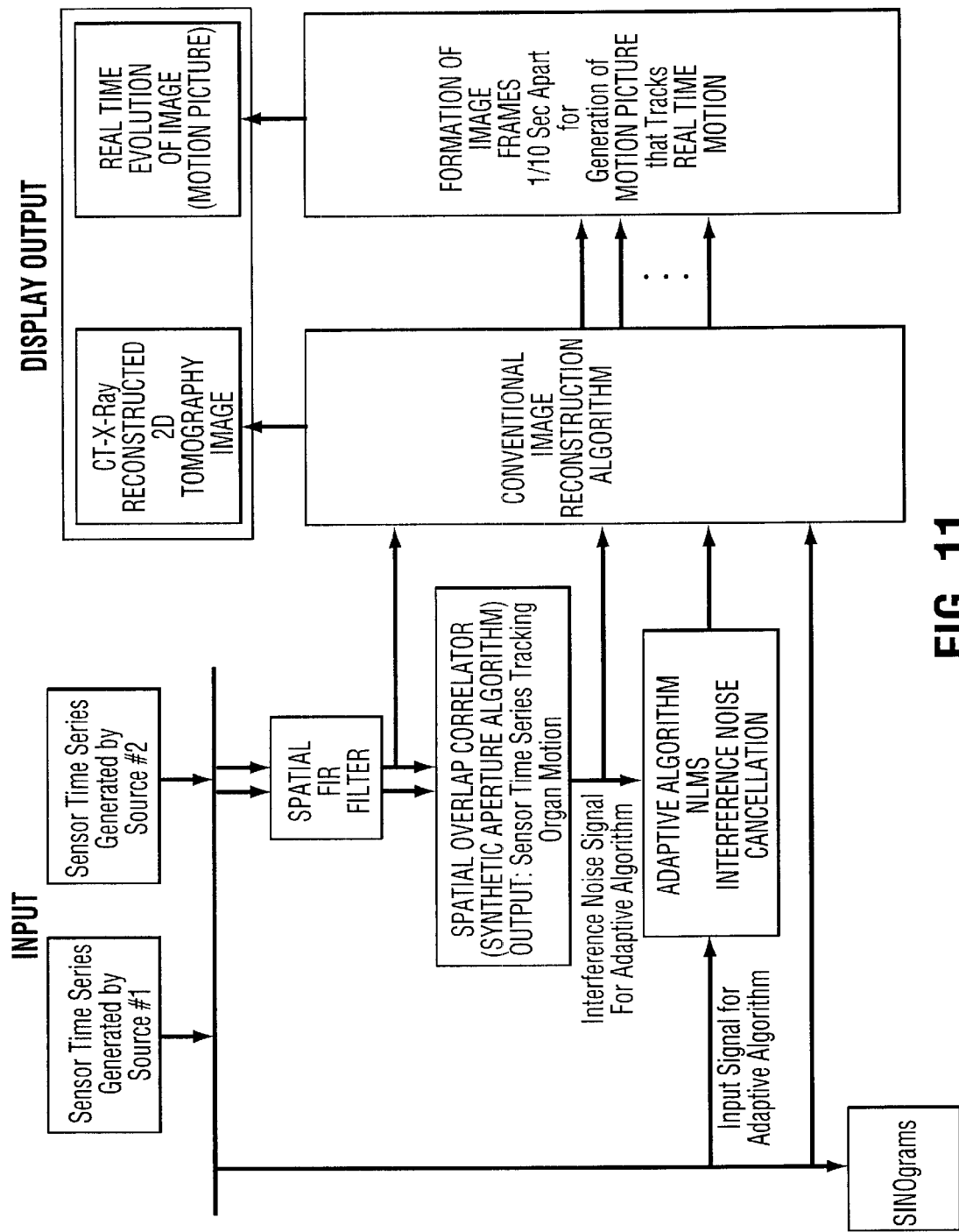
FIG. 11 is a schematic diagram of an implementation of a method for tracking organ motion, a method for removing motion artifacts and a method for generating a motion picture according to the invention.

FIG. 11 illustrates a signal processing flow diagram for an implementation of the spatial overlap correlator method, the adaptive processing method and the method for generating a motion picture within current processing schemes for X-ray CT systems according to the invention. The signal processing methods according to the invention are indicated by shaded blocks, whereas current processing schemes for CT systems are indicated by unshaded blocks. For example, sensor time series generated by source #1 and/or source #2 are processed using a spatial finite impulse response (FIR) filter. The sensor time series may then be processed using a conventional image reconstruction algorithm or, preferably, processed using the spatial overlap correlator method for providing information due to organ motion. The resulting information is then used as interference noise signal for removing motion artifacts from the sensor time series using the adaptive processing method. The resulting sensor time series is then processed using the conventional image reconstruction algorithm to produce a reconstructed image for display. Alternatively, the resulting information is processed by the conventional image reconstruction algorithm to provide reconstructed images containing only information of moving components. Furthermore, CT scan data acquired within a long time period such as 30 seconds may be processed to obtain a motion picture.

In the following, a software approach of the spatial overlap correlator method will be disclosed. The Software Spatial Overlap Correlator (SSOC) method according to the invention is based on the fact that the image sampling process of a CT scanner is periodical, therefore, image samples taken at a time t and at a time t+T are taken from identical spatial locations. In the SSOC method image samples separated by a time interval T are compared, obviating irradiation of an object using two sources as shown in FIG. 2. This allows retrofitting of most of existing CT scanners without major hardware modification. Therefore, this method provides the advantages of tracking organ motion and removing motion artifacts as an upgrade for existing CT scanners at a relatively low cost.

Figure 12C:
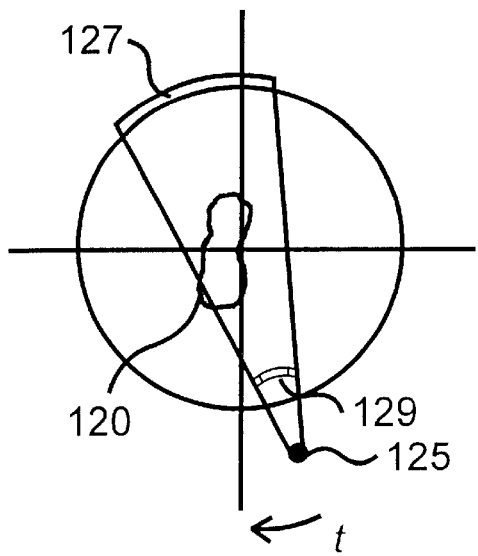
Figure 12C:
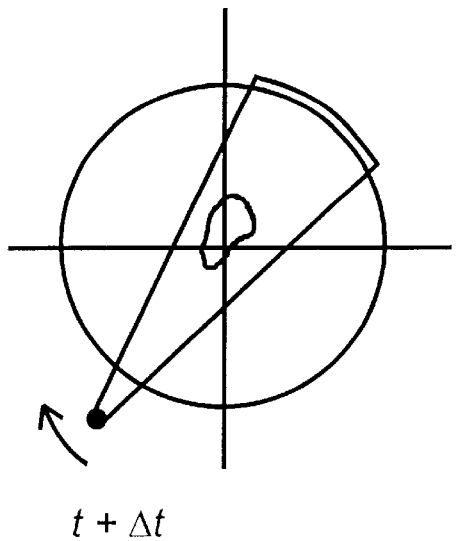
Figure 12C:
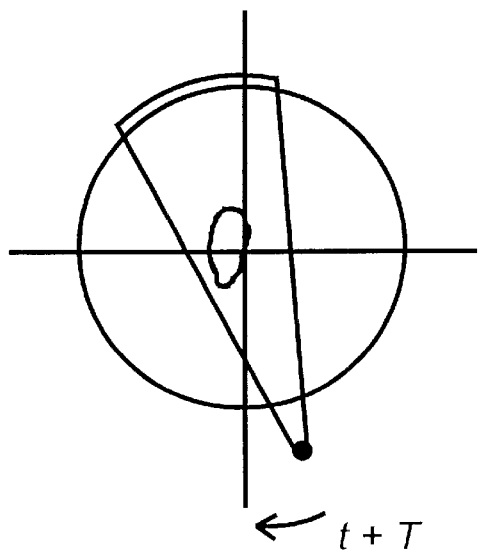
Figure 12D:
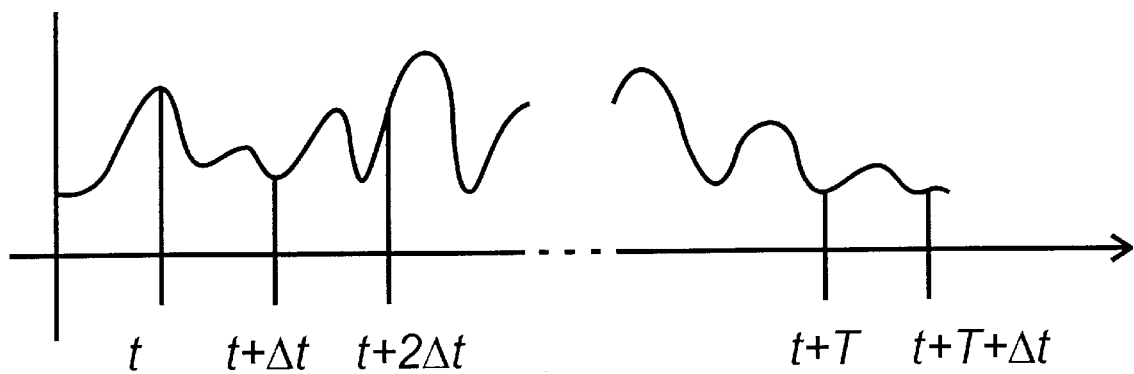
FIG. 12d illustrates a sensor time series provided by a conventional CT scanner.

FIGS. 12a–12c show the image sampling process using a conventional CT scanner comprising one source 125 for irradiating an object 120. The source 125 and a receiving sensor array 127 are rotated in step increments of $\Delta t$ around the object 120 providing a sensor time series as shown in FIG. 12d. At times t and t+T images are sampled from an identical spatial location. In order to obtain information associated with the organ motion - motion of the object 120—during the data acquisition process, samples separated by a time interval T are compared using the SSOC method according to the invention.

For simplicity, the sensor time series as shown in FIG. 12*d* will be considered a sinusoidal function. As is evident to a person of skill in the art this assumption does not imply a loss of generality because any signal can be expressed as a series of sinusoidal functions. To track motion of the object 120 the difference between the signals at time t and t+T is determined. The difference between two sinusoidal varying signals of a same frequency but different phase yields a new sinusoidal signal of the same frequency but different phase:

$$\sin(2\pi f_0 t) - \sin(2\pi f_0(t+t_0)) = -2\left[\sin(\pi f_0 t_0)\cos\left(2\pi f_0\left(t+\frac{t_0}{2}\right)\right)\right]. \quad (9)$$

Figure 13:
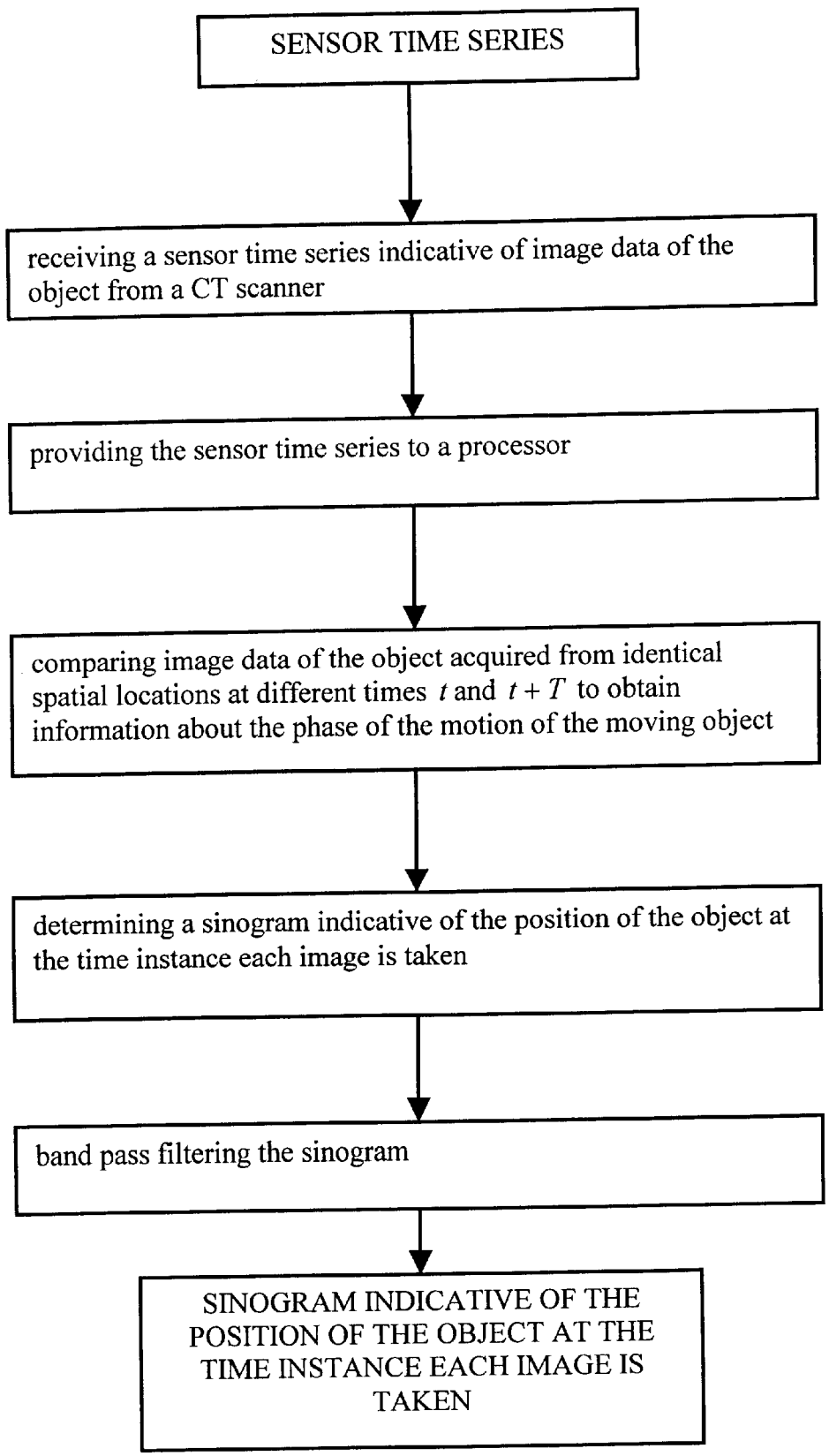
FIG. 13 is a schematic diagram of a software spatial overlap correlator method according to the invention.

It is evident from equation (9) that the difference of a periodic signal and a delayed version of this signal yields a signal of the same frequency but different phase. The SSOC analysis of the sensor time series as described in equation (9) provides information about the phase of the motion of the moving object 120. Therefore, the waveforms of the sinogram obtained by the SSOC method according to the invention, as shown in FIG. 13, indicate the position of the object 120 at the time instance each image is taken.

The relationship expressed in equation (9) holds if the product $(f_0 t_0)$ is not an integer. The product $(f_0 t_0)$ is an integer if the periodicity of the object motion and the periodicity of the image sampling are exactly a same. In this case the SSOC method does not track the object motion and the object appears stationary. For example, in cardiac x-ray CT imaging applications this occurs in exceptional cases where the period of the cardiac cycle coincides exactly with the period of data acquisition of the CT scanner.

Figure 14:
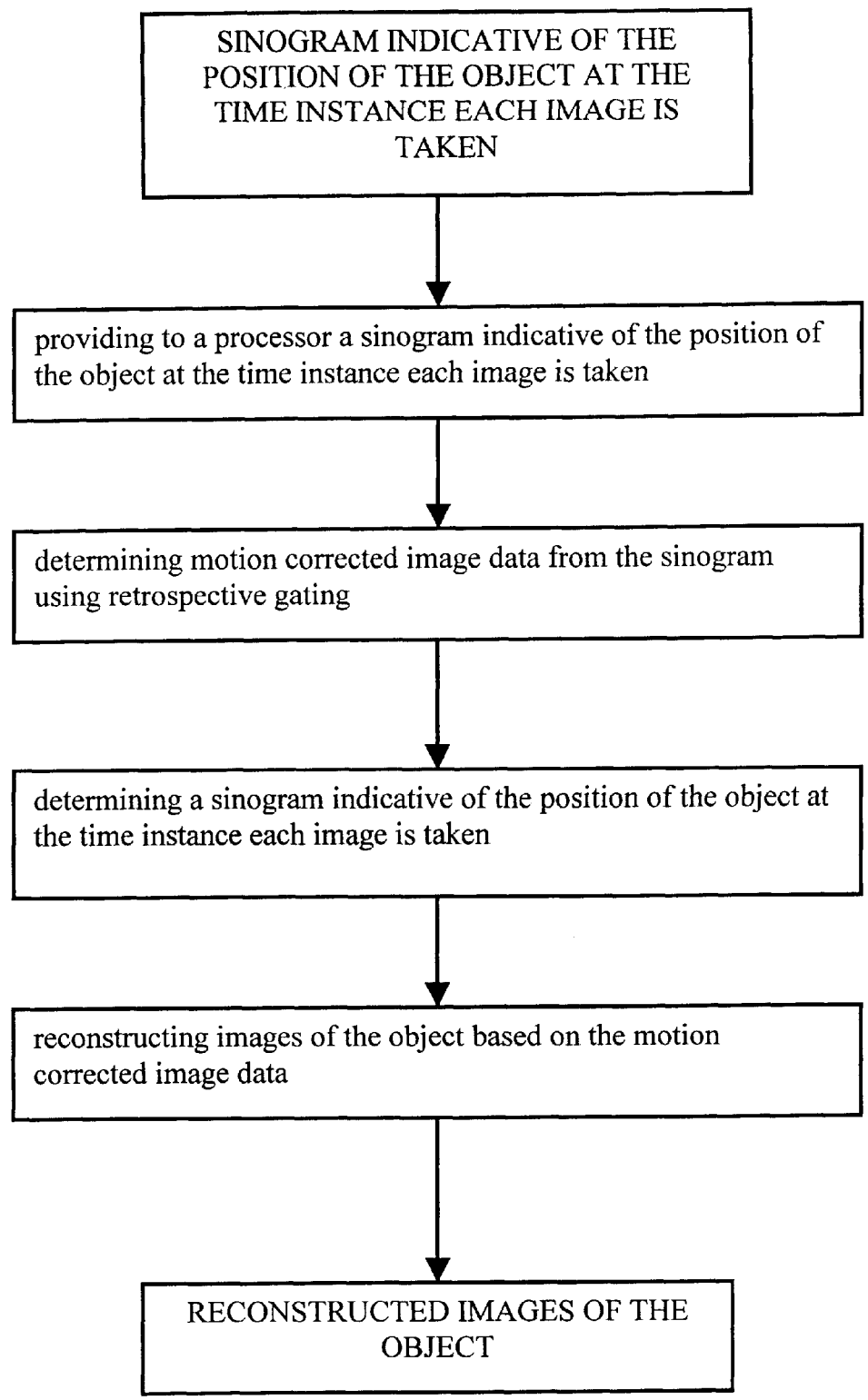
FIG. 14 is a schematic diagram of a method for motion correction according to the invention using retrospective gating.
Figure 15:
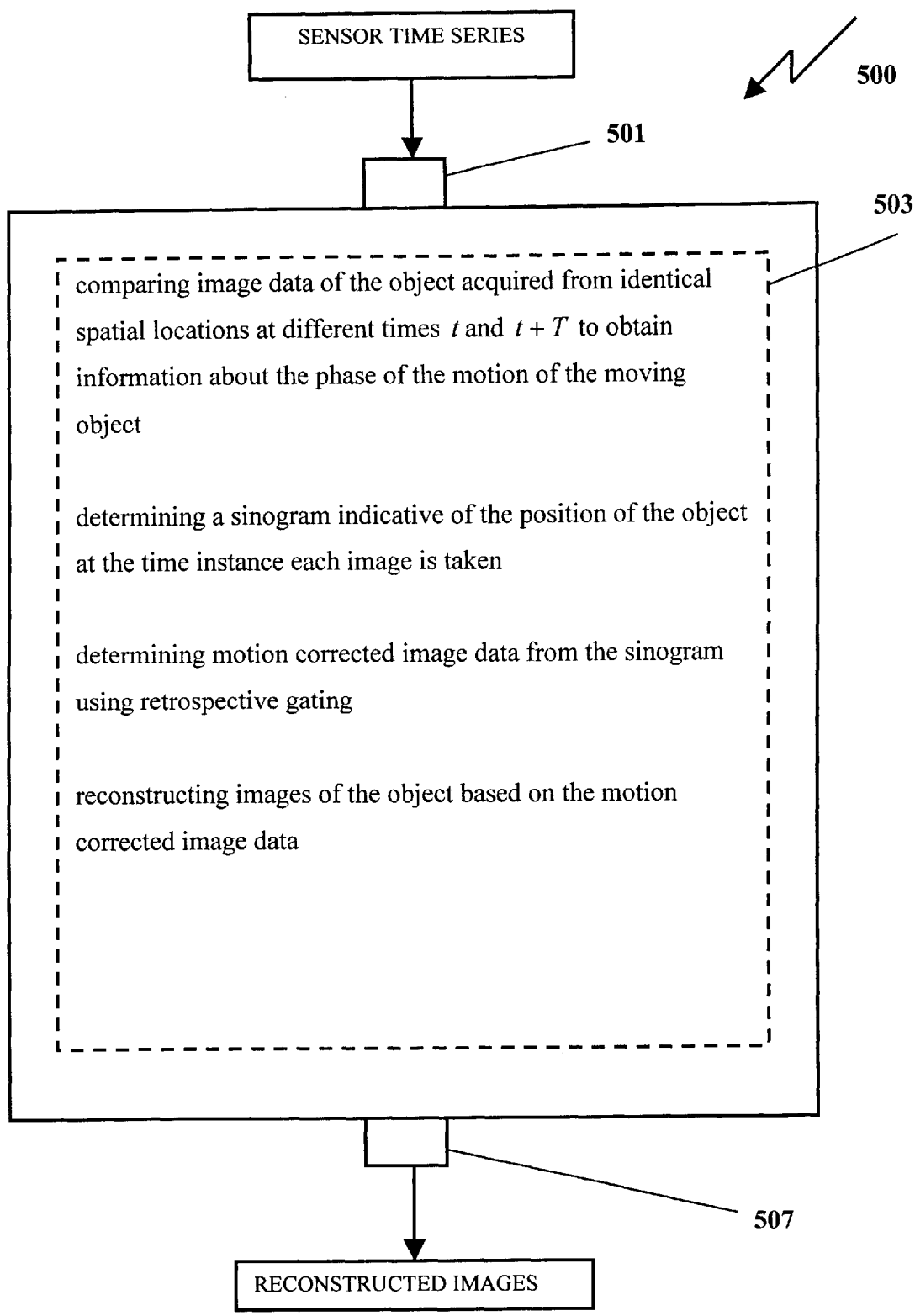
FIG. 15 illustrates an image data processing system according to the invention.

In "Gated cardiac computed tomography with a motion phantom," Radiology 134 [1]213–7 (1980), Morehouse et al. disclosed a motion correction technique for x-ray CT cardiac imaging applications based on retrospective ECG gating, which is included hereby for reference. The technique comprises continuous acquisition of projection image data during a few rotations of the x-ray source and selecting projection image data during a specified window of the cardiac cycle, during diastole when the heart is moving the least. Thus monitoring cardiac motion by integrating an ECG system with the CT scanner was an essential requirement for applying this method. The waveforms of the sinogram provided by the spatial overlap correlator track the cardiac motion and can, therefore, be used to identify phases of motion. In the RG-SSOC method for motion correction according to the invention, shown in FIG. 14, retrospective gating as disclosed by Morehouse et al. is applied using the waveform provided by the SSOC for identifying the phase when the heart is moving the least. Based on the identified phase a segment—180 degrees plus a fan angle 129—of the sinogram provided by the SSOC is then selected for image reconstruction. Therefore, applying retrospective gating RG to the output of the SSOC eliminates the requirement for system integration of ECG systems with a CT scanner. This is a highly advantageous feature if existing CT scanners have to be retrofitted for motion correction, in particular, for cardiac imaging applications. Referring to FIG. 15 an image data processing system 500 for tracking motion present during computer tomography scan data acquisition of an object according to the invention is shown. Sensor time series indicative of image data of the object are received via a port 501 from a conventional CT scanner. The data are then processed using processor 503 according to the RG-SSOC method. Reconstructed image data are then provided via a port 507 for further processing, for example, displaying on a monitor.

Figure 16:
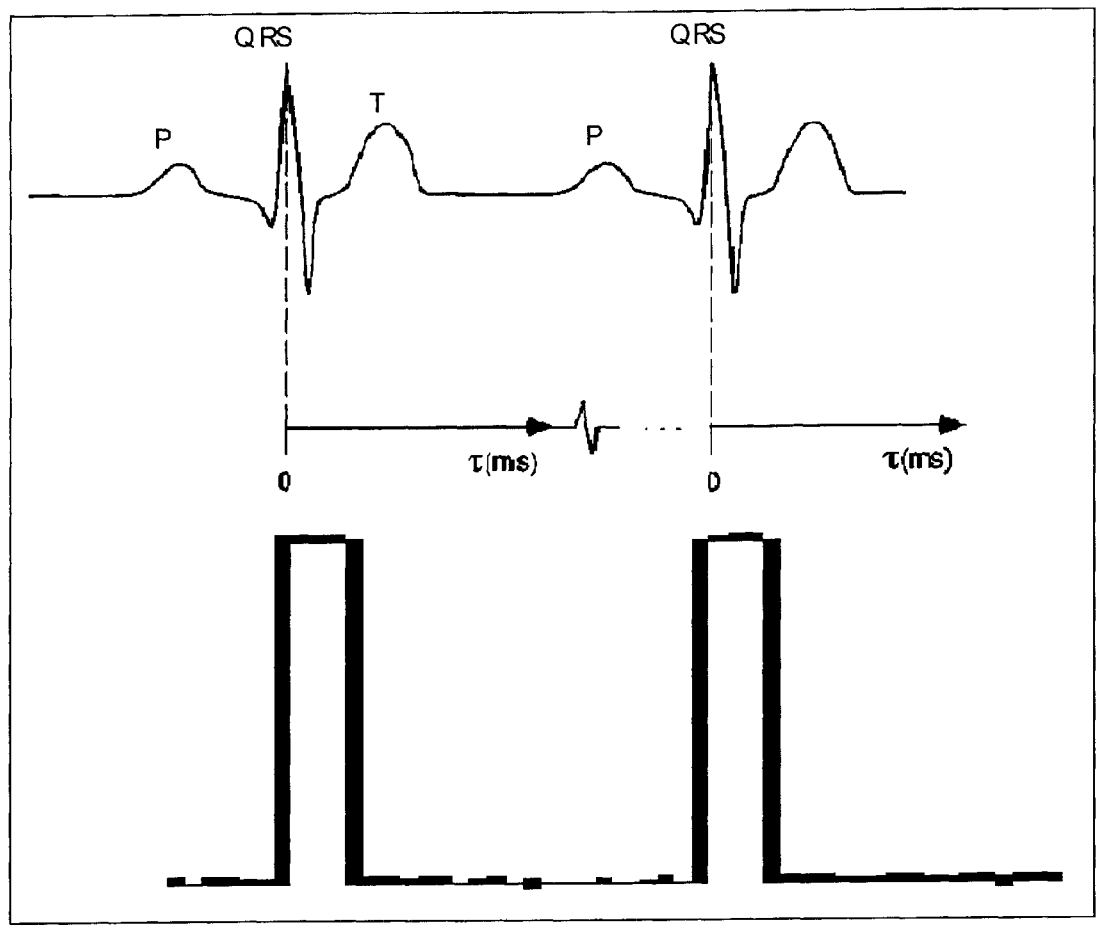
FIG. 16 illustrates synchronization between ECG waveforms and a starting point of recording of projection data from a CT scanner.
Figure 17A:
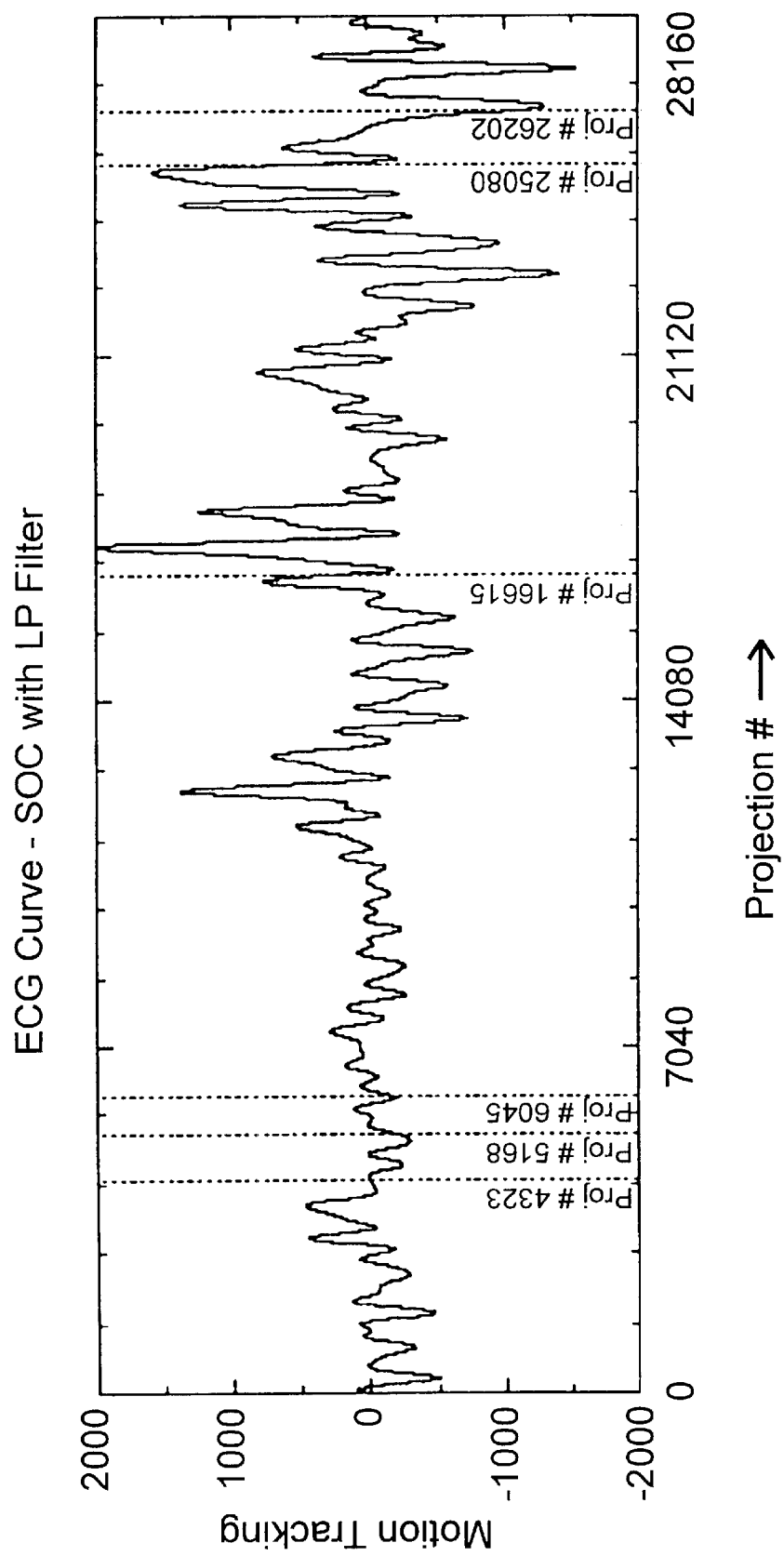
FIGS. 17a–17c show synchronized outputs of the software spatial overlap correlator and the ECG.
Figure 17B:
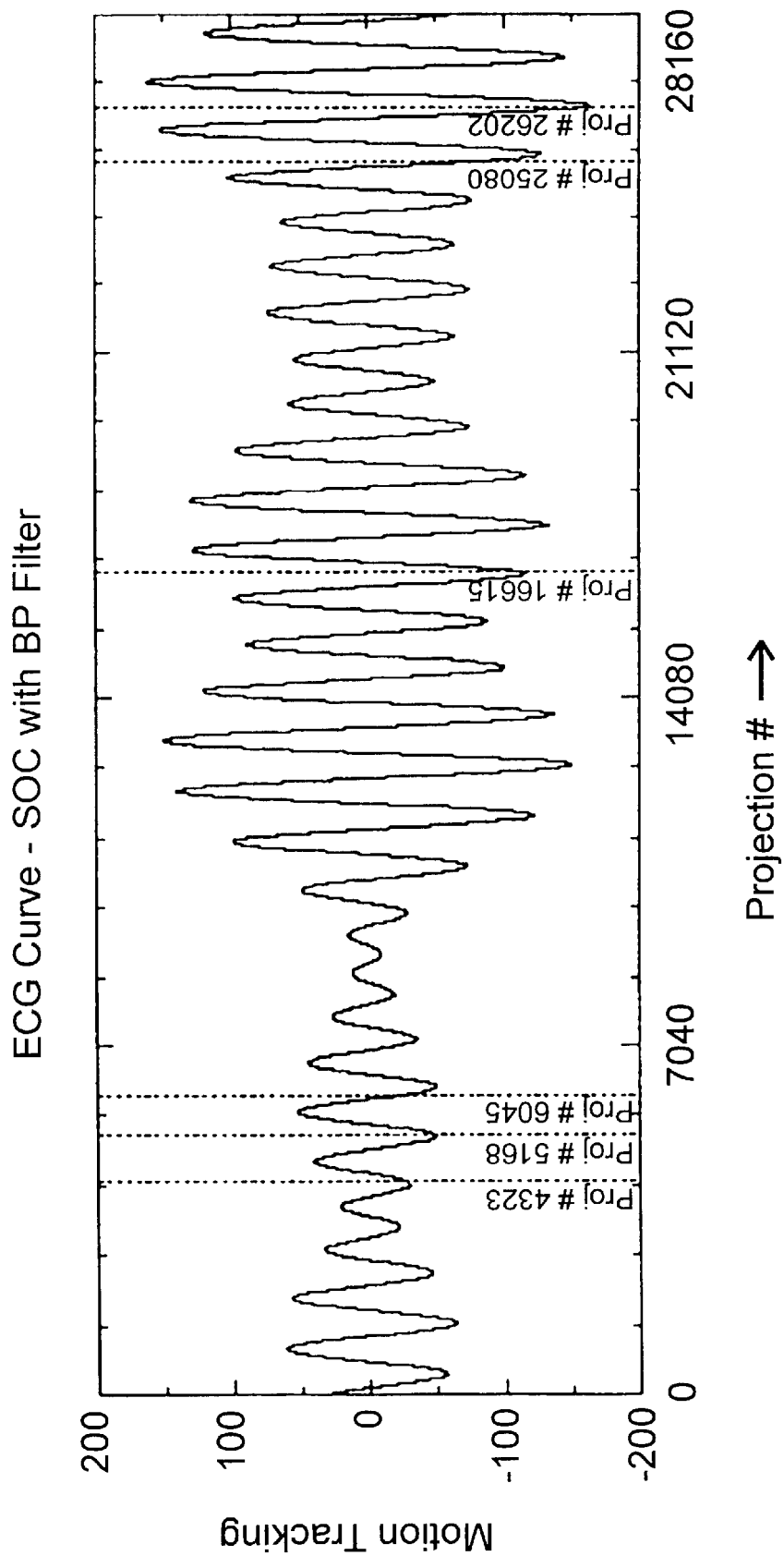
Figure 17C:
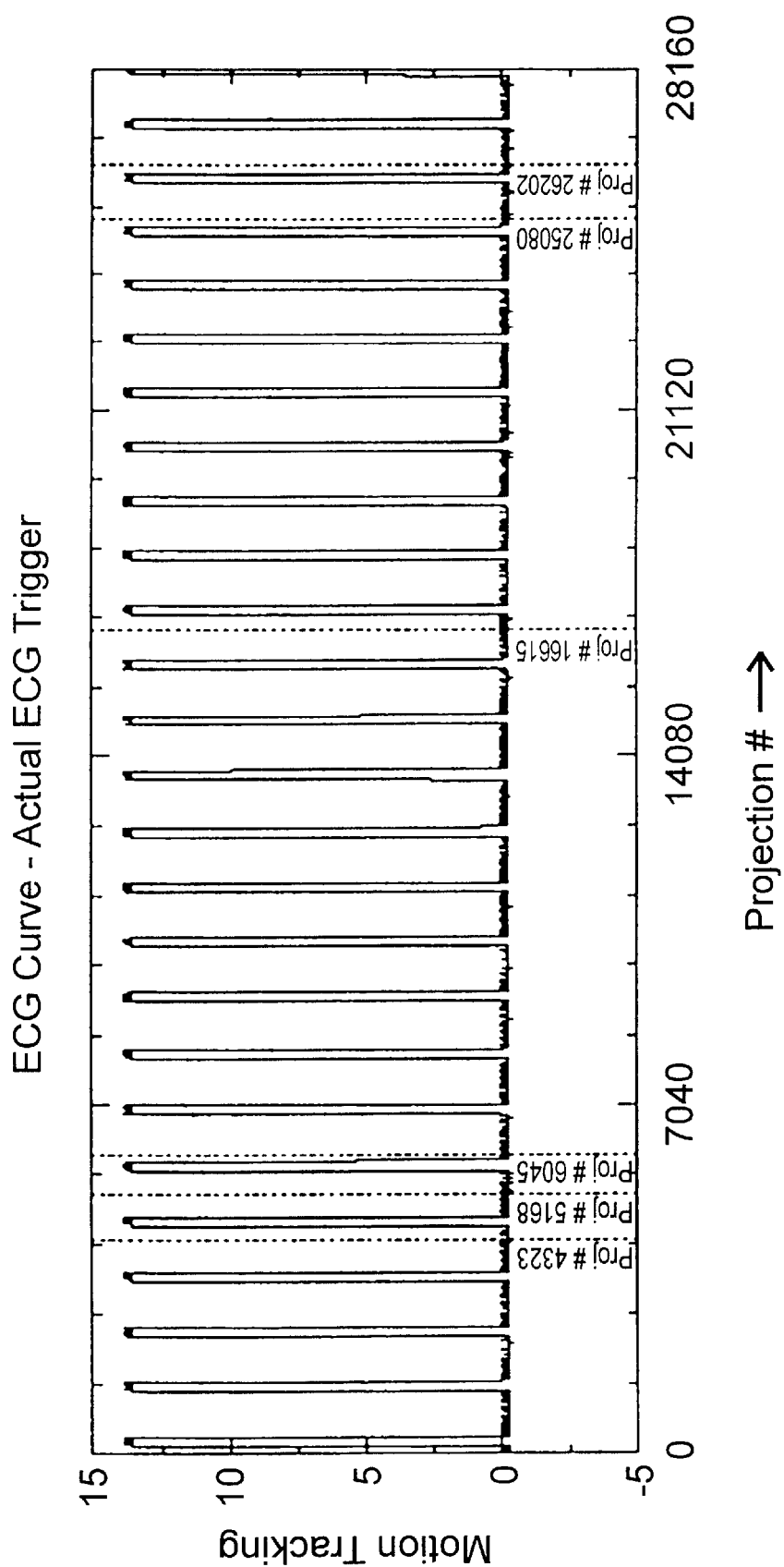

In a set of clinical tests the RG-SSOC method for motion correction according to the invention has been compared with the retrospective ECG-gating process of Morehouse. Therefore, the data acquisition process required synchronization between the ECG waveforms and the starting point of recording of projection data from the CT scanner as shown in FIG. 16. The upper part of FIG. 16 presents an ECG waveform and the lower part the triggering signals sent from the ECG system to the scanner. The first square pulse signaled the start of the acquisition process of projection data. FIGS. 17a–17c show the synchronized outputs of the SSOC and ECG triggering signal that allowed the comparison of both gating methods using a same set of data. The CT scanner was positioned such that images of the ventricles of the lower part of a patient's heart were obtained. During the data acquisition process the patient was asked to follow breath holding procedures. FIG. 17a shows the output of the SSOC indicating a complex spectrum of frequencies. The following diagram shows the band-pass filtered output of the SSOC waveform centered on the frequency of the patients heart beat rate of 75 bpm. The lower diagram shows the ECG triggering signals that were used as reference to choose segments of the sinogram for the retrospective ECG gating. The segments of the sinograms were chosen from a section between the T and P phases of the ECG waveform as shown in FIG. 16, which represents the diastole phase when the heart is moving the least. Vertical lines crossing all three diagrams in FIGS. 17a–17c indicate the starting point of the sinogram segments chosen for image reconstruction. The properties of the patient's heart motion are immediately obvious in the curves provided by the SSOC shown in the upper two diagrams of FIGS. 17a and 17b. These curves allow computing of the actual period of the heart motion, which is approximately 0.73 seconds. Furthermore, the SSOC sinograms reveal a significant increase in the amplitude of the patient's overall movement during the CT data acquisition process. This is an indication that the patient was not able to maintain breath hold and started to gasp. The band pass filtered SSOC sinogram reveals two very close frequencies in the spectrum separated by approximately 0.19 Hz as indicated by the beating effect. Since the SSOC sinogram tracks the motion of the heart's two ventricles it is evident by the two close frequencies that the two ventricles are not synchronous. This observation is clinically correct since the patient was 65 years of age and had a weight above 150 kg.

Figure 18:
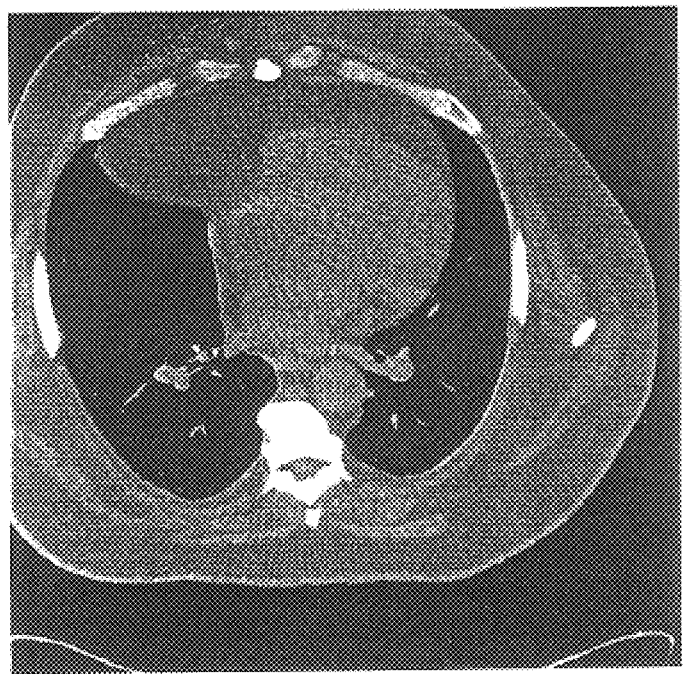
FIG. 18 shows a reconstructed image using retrospective ECG gating for motion correction.
Figure 19:
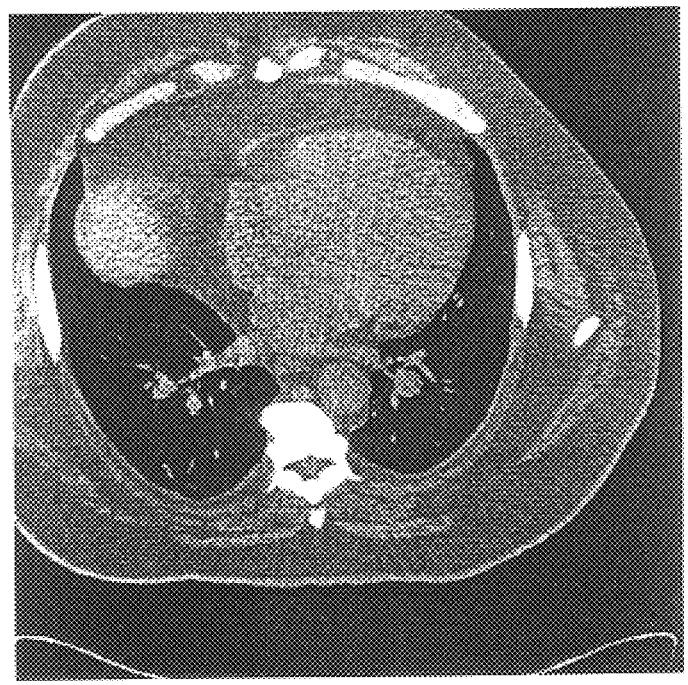
FIG. 19 shows a reconstructed image using retrospective ECG gating for motion correction.
Figure 20:
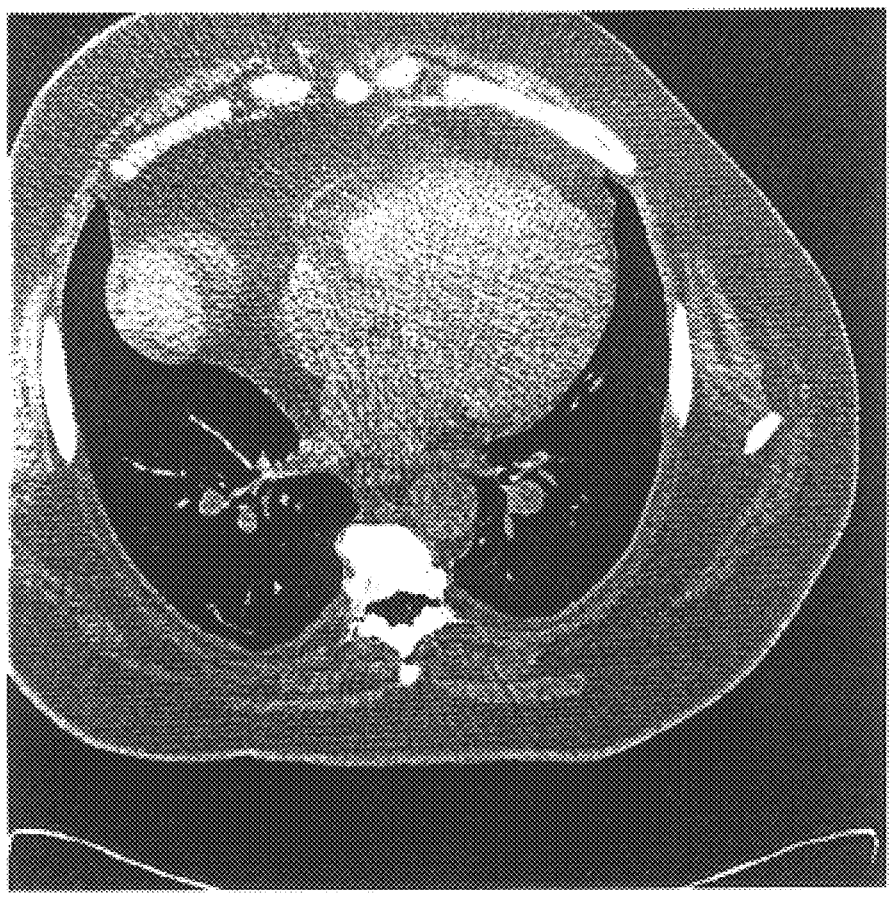
FIG. 20 shows a reconstructed image using retrospective RG-SSOC gating according to the invention for motion correction.

FIG. 18 shows a reconstructed image using retrospective ECG gating for motion correction. The projection point #26202, shown in FIG. 16 defines the starting point of the sinogram segment used for image reconstruction. This starting point of the sinogram segment defines an area with large motion effects due to patient's gasping as is evident from the SSOC sinogram. This observation suggests that motion artifacts should be present in the corresponding reconstructed image. However, the ECG signals in the lower diagram of FIG. 16 suggest that the same point #26202 should provide a window for retrospective ECG gating with minimum motion effects in the corrected image. Comparison of the image shown in FIG. 18 with an image reconstructed using a sinogram segment with little motion effects starting at projection #6045, shown in FIG. 19, provides evidence of these motion effects resulting in an reconstructed image of substantially inferior image clarity. These results suggest that the SSOC process is very accurate for identifying characteristics of the heart's localized motion where the imaging took place, which cannot be detected by an ECG. FIG. 20 shows the image results of motion correction using the RG-SSOC gating method according to the invention. For reconstructing the image a sinogram segment starting at projection point #4323 shown in FIGS. 17a–17c was chosen. According to the ECG signals this projection point includes the QRS phase of the ECG waveform suggesting the strongest heart motion effects. However, for the same projection point #4323 the SSOC waveform indicates very small amplitude motion for the imaged section of the lower part of the heart's ventricles. Motion effects are minimized in the corrected image using the RG-SSOC method as is evident from the reconstructed image shown in FIG. 20. For example, the thickness of the heart's pericardium as well as the boundaries of the ventricles can be identified with better clarity as in FIG. 19.

The RG-SSOC method according to the invention provides superior results compared to the ECG gating method due to the fact that the SSOC process tracks motion effects localized in the imaged area, an ECG system is not designed to track. Furthermore, the method according to the invention is able to track motions other than cardiac motion and is, therefore, able to provide motion correction for imaging of other organs than the heart and allows, for example, to correct motions due to a patient's breathing. This allows a patient to breathe freely during a CT data acquisition process, increasing patient convenience and avoiding gasping motion effects that become dominant towards the end of a 3D CT data acquisition process. For clinical implementation the RG-SSOC method requires continuous projection data from only 1.5 to 2 rotations. This allows the SSOC to track the motion amplitude and to identify the phase corresponding to the smallest motion amplitude in order to select a sinogram segment for image reconstruction.

Figure 21:
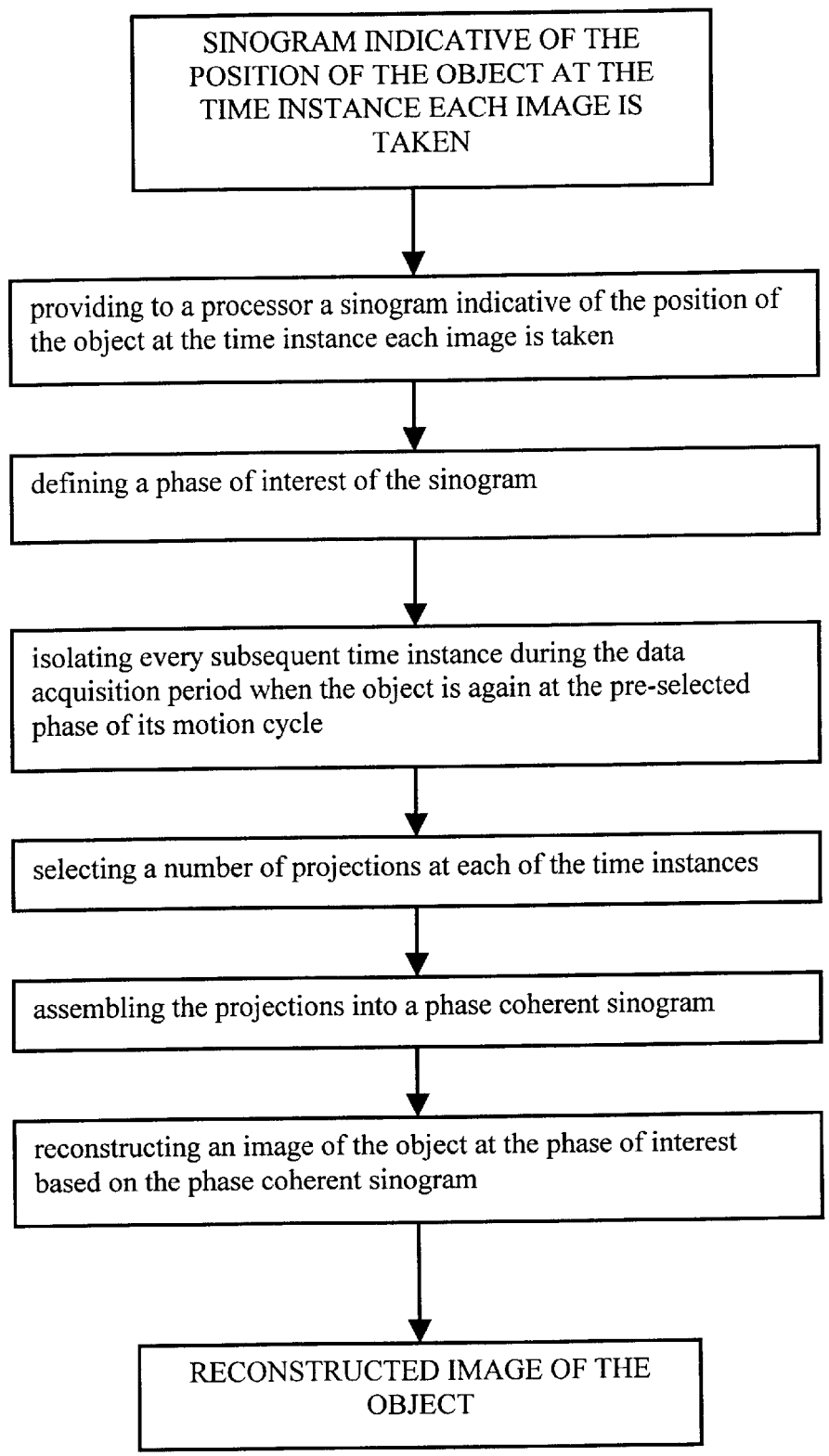
FIG. 21 is a schematic diagram of a method for motion correction according to the invention using coherent sinogram synthesis.

Analysis of the sinograms provided by the SSOC provides information about the phase of the motion of a moving object or organ. In other words, these time series provide information about the position of the object at the time instance each view is taken. This information is the basis for the coherent sinogram synthesis CSS method according to the invention, as shown in FIG. 21. The sinograms provided by the SSOC allow the construction of a new coherent sinogram that is synthesized using only views that correspond to a single point in phase of the motion. Image reconstruction based on the synthesized sinogram produces an image depicting the moving object frozen at the single point in phase. The CSS method does not require any kind of periodicity for the motion effects. It requires only repetition of the selected phase of motion.

First a specific phase of interest of the sinogram provided by the SSOC is defined. Every subsequent time instance during the data acquisition period when the object is again at the pre-selected phase of its motion cycle is then isolated, as shown in FIG. 22. A number of projections at each of these time instances are then selected and assembled into a phase coherent sinogram.

Selection of the in phase information of the motion cycle detected by the SSOC process is provided by sliding window correlation processing. In general, the cross-correlation coefficient $CC_{sr}$ between two time series $s_i$ and $r_i$ of length L is given by equation (10).

$$CC_{sr} = \frac{\sum_{i=1}^{L} s_i r_i}{\sqrt{\sum_{i=1}^{L} s_i^2 \sum_{i=1}^{L} r_i^2}} \quad (10)$$

The sliding window correlation technique uses a subset $r_i$ of the signal near the phase of interest as a replica, and correlates this replica with segments of continuous signal sito compute a time varying correlation function. The segments of the signal used in the cross-correlation function are selected in a sliding window fashion. The time varying cross correlation function $CC_i$ is given by equation (11), $$CC_i = \frac{\sum_{j=-L/2}^{L/2} s_{i+j} r_{j+L/2}}{\sqrt{\sum_{j=-L/2}^{L/2} s_{i+j}^2 \sum_{j=-L/2}^{L/2} r_{j+L/2}^2}}, \quad i = \frac{L}{2}, \frac{L}{2}+1, \ldots, N-\frac{L}{2} \quad (11)$$

where L is the length of the segment used in the cross correlation function and N is the length of the complete sinogram provided by the SSOC.

Figure 22A:
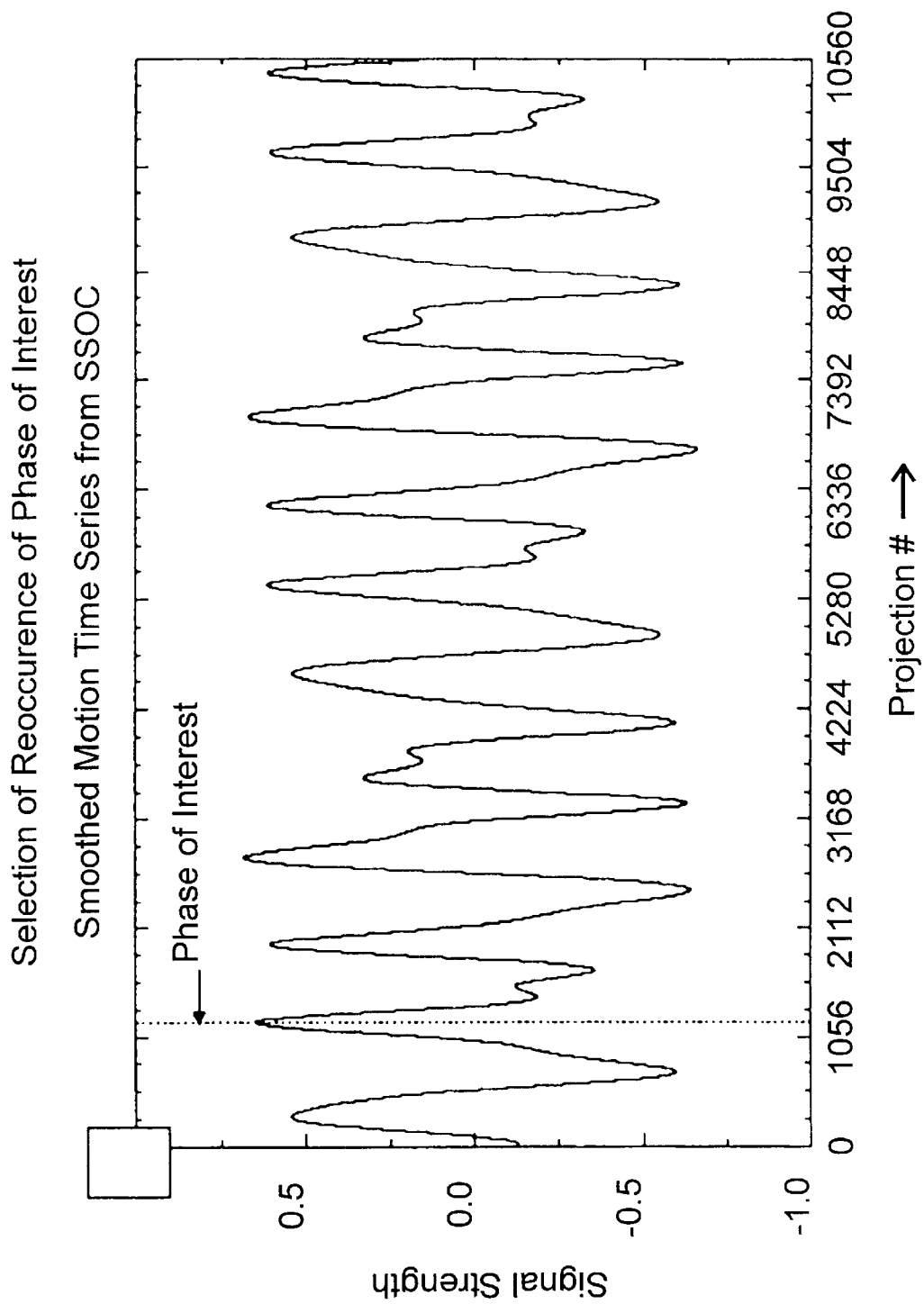
FIGS. 22a and 22b are schematic diagrams illustrating the selection of a phase of interest by correlation according to the invention.
Figure 22B:
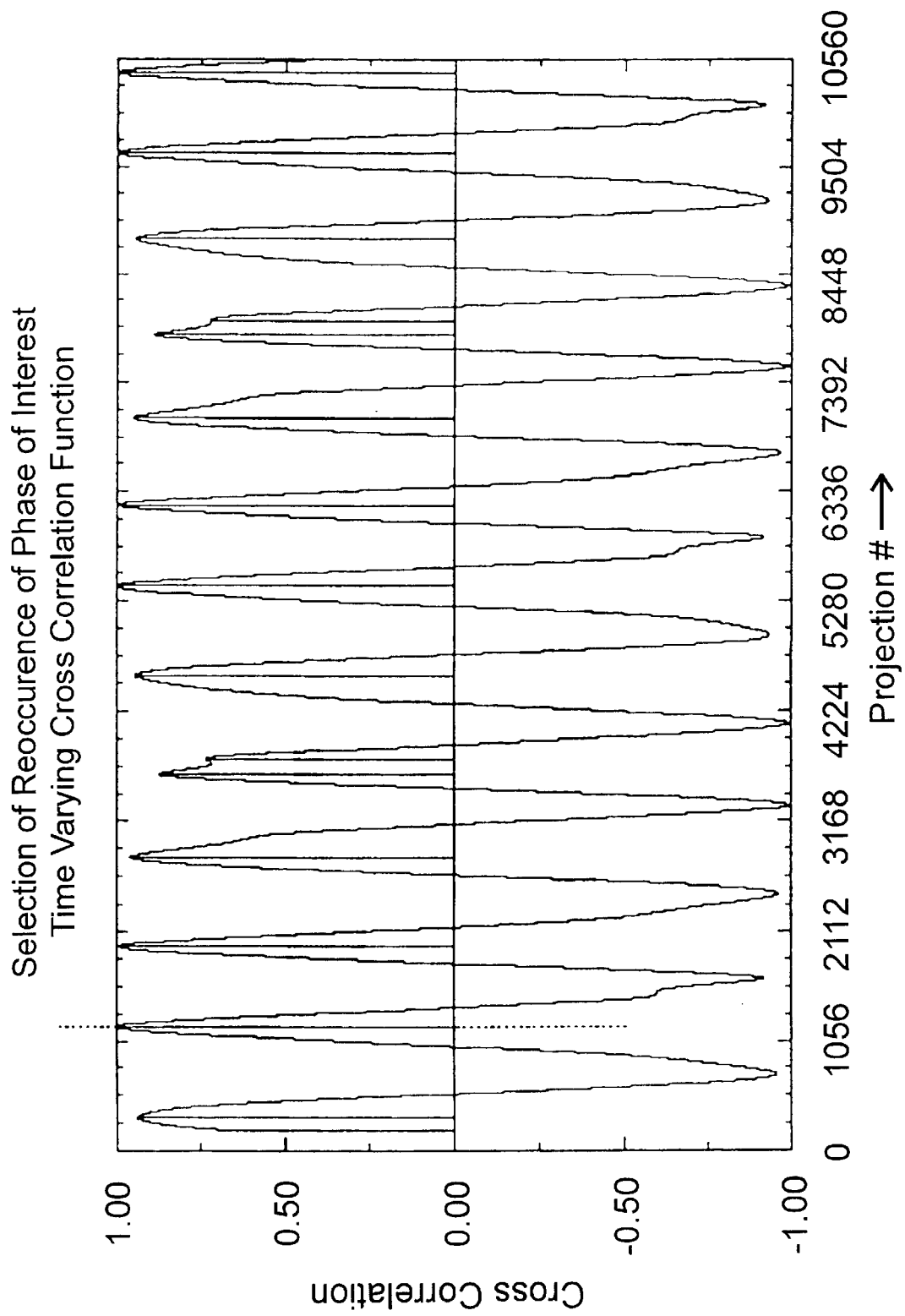
Figure 23:
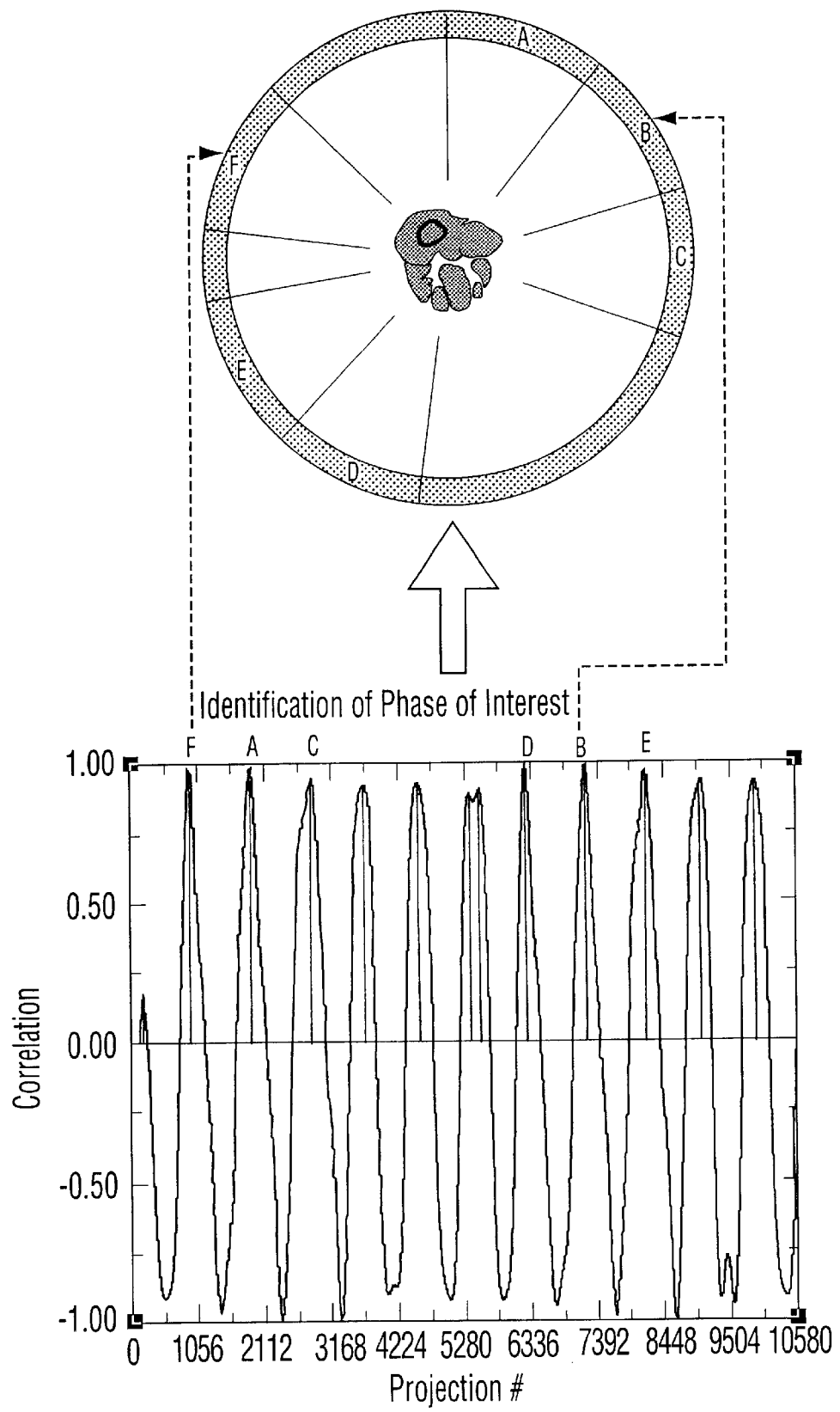
FIG. 23 is a schematic diagram illustrating the operation of the coherent sinogram synthesis method according to the invention.

FIG. 22a shows the smoothed sinogram obtained from the SSOC with the phase of interest marked. Using a replica centered at the point marked as the phase of interest the time varying correlation function is shown in FIG. 22b. From the time varying correlation function, it is evident that the level of correlation between the replica and the sinogram, which describes the organ motion, reaches a maximum value of approximately one whenever the phase of interest reoccurs. The vertical bars in the curve of FIG. 22b indicate the detected maxima. The time instances where these maxima are in the range of $(0.8 < CC_i \leq 1.0)$ are considered as the time instances at which the phase of interest reoccurs. The time instances directly define a projection number since the projections acquired sequentially at a known sampling rate. A coherent sinogram, as shown in the diagram in FIG. 23 is then assembled using all these projections. The selected time instances map to angular locations determined by the location of the CT source and the detector array at the time instances of the selected phase of the periodic organ motion as shown in FIG. 23. Since the data acquisition of a CT scanner is circular, all of the spatial locations are sampled repeatedly. A projection number P and p is given by the circular mapping in equation (12), $$P = mM + p, \ 0 \leq P \leq \infty, \ 0 \leq p \leq M, \ m = 1, 2, \ldots, \infty \quad (12)$$

where M is the number of projections taken by the CT scanner in a single rotation. The selected segments of a sinogram are synchronized to the organ motion cycle, in that valid projections are only obtained when the organ is at the desired point in its motion cycle. Under ideal conditions, one view is taken at each time instance the organ reaches the desired point and after N cycles of motion a complete sinogram is obtained.

Since there is no synchronization between the data acquisition process and the organ motion some views are repeated and some views are still missing. Therefore, an interpolation process is required to calculate missing angular segments as shown in FIG. 23. Standard interpolation methods such as cubic-spline interpolation are successful at interpolating large structures, which are well defined in the sinograms.

However, they are not capable of interpolating small spatial structures, for example, those associated with cardiac imaging applications. The interpolation techniques used in the CSS method use data from one complete revolution of the CT scanner as a basis for the coherent synthesis of the sinogram. Using the sinogram of the one complete revolution of the CT scanner as a starting point, fixed sized projection windows are selected as described above. Whenever a suitable projection window is found it is used to overwrite the original projections of the original sinogram. This method is useful if the image quality is sufficiently good, since it modifies the original sinogram to obtain an improved image. Another interpolation technique used in the CSS method is based on a flexible window approach. Here, the sizes of the selected segments of projections are allowed to be as large as necessary to fill the entire sinogram. The center of the initial segment of projections is defined as an ideal point. The missing projections are then filled in using appropriate projections from the acquired data such that each projection is as close as possible to an ideal point. This method is preferred when the image quality is poor.

Figure 24:
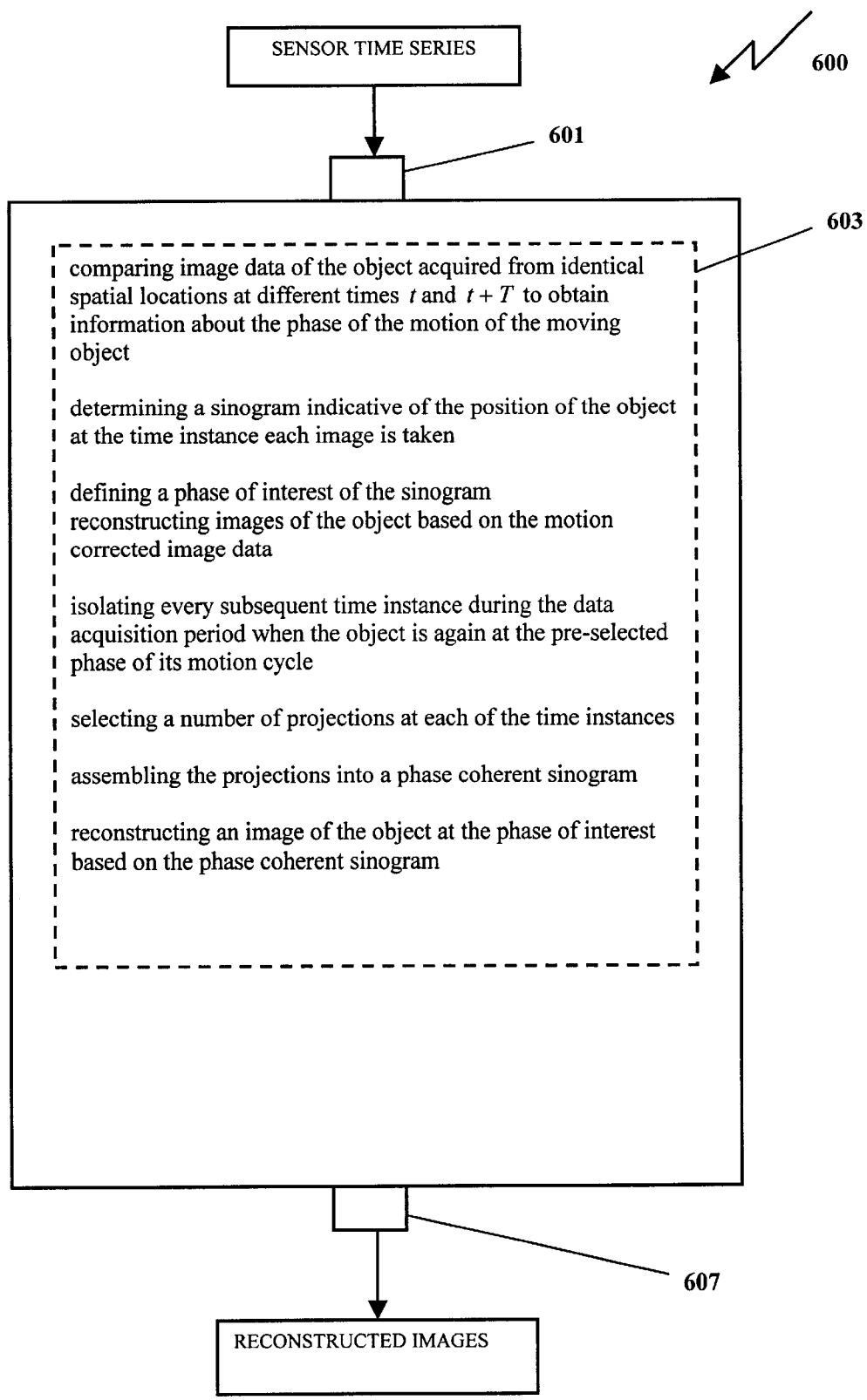
FIG. 24 illustrates an image data processing system according to the invention.

Once a coherent sinogram for a single phase of organ motion is complete, the image is obtained using conventional image reconstruction processing, which is equivalent to that of a stationary object. FIG. 24 illustrates an image data processing system 600 for tracking motion present during computer tomography scan data acquisition of an object according to the invention. Sensor time series indicative of image data of the object are received via a port 601 from a conventional CT scanner. The data are then processed using processor 603 according to the SSOC and CSS methods. Reconstructed image data are then provided via a port 607 for further processing, for example, displaying on a monitor.

The CSS method requires a data set to be acquired over more than one revolution of the CT scanner. The number of revolutions is depending on the desired image quality. The correctness of the synthesized sinogram to the equivalent sinogram of a stationary object is directly related to the length of the acquired data sequence. This correctness is also a function of the speed of the object's motion. Generally, a faster moving object will yield a more correct sinogram than a slow moving object for a fixed length data sequence, because there are more cycles available.

Figure 25:
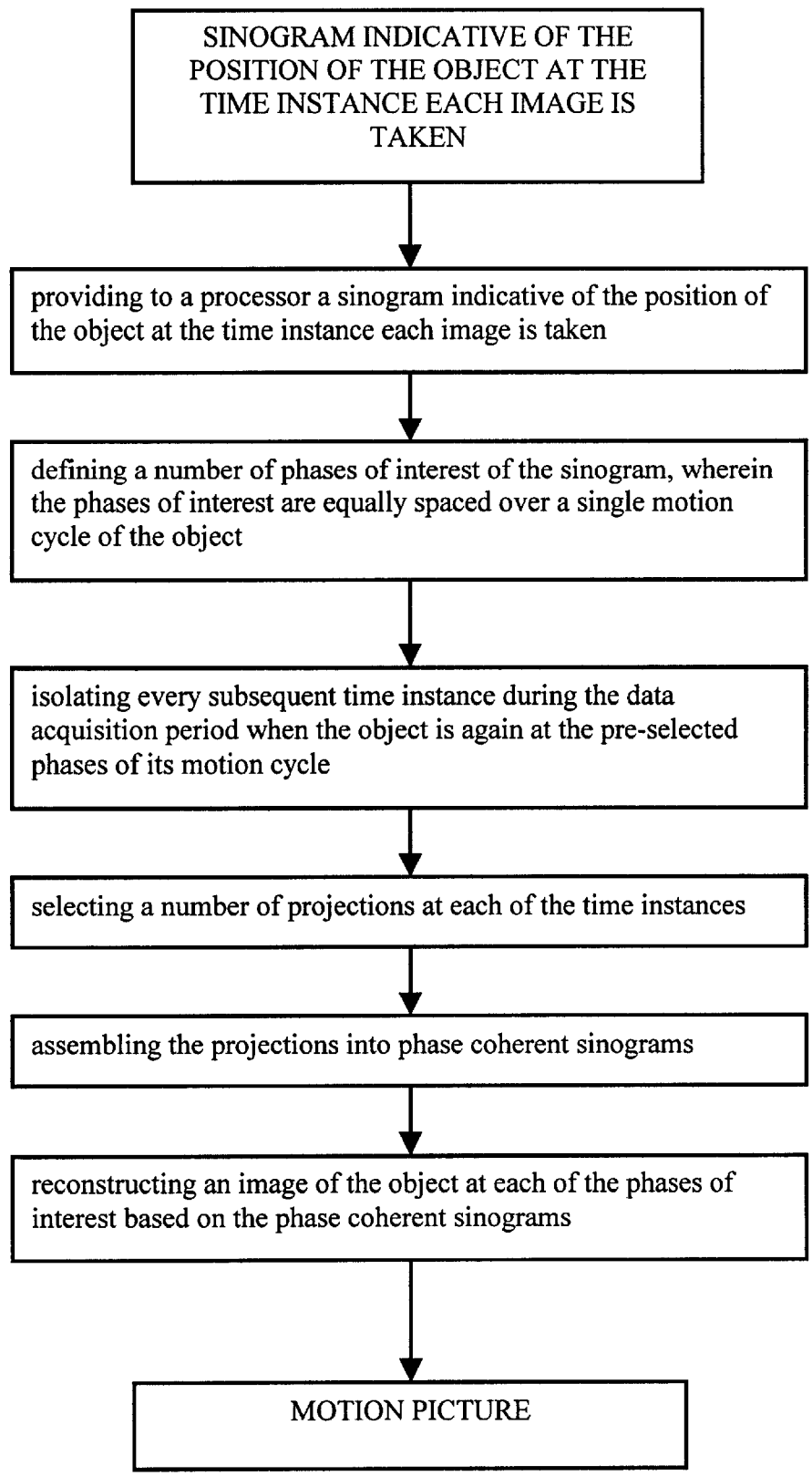
FIG. 25 is a schematic diagram of a method for generating phase coherent motion pictures according to the invention using coherent sinogram synthesis.

An advantage of the CSS method is the ability to generate phase coherent motion pictures, as shown in FIG. 25. A number of phases of interest are selected, equally spaced over a single motion cycle of the object and an image is created for each of these points. These images in the correct order provide the frames of a CT motion picture showing the moving object as it goes through various phases of its motion cycle.

FIG. 26 shows a conventional CT image with the heart at the center. Lung structure characteristics are also shown at both sides of the heart with a tumor at the top left side of the heart. Clarity of this image suffers from artifacts due to breathing effects, which are evident at the area near the sternum, and cardiac motion artifacts, which are indicated by the substantial distortion of a white dot near the top right area of the heart. FIG. 27 shows the corresponding image to FIG. 26 but with motion correction using the SSOC and CSS methods. In this case, motion artifacts due to breathing effects have been removed as indicated by the clarity of the image near the area of the sternum. Another improvement of diagnostic importance is the better and brighter definition of the white dot clearly indicating cardiac blood vessel calcification at the top right area of the heart. Thus, the overall image quality of FIG. 27 is significantly better than the conventional CT image.

The real data sets for testing the Software Spatial Overlap Correlator have been acquired using a Siemens x-ray CT Somatom 4 medical imaging system. In particular, the simulations included a T=0.75 seconds period of rotation for the CT system with a set of M=1056 projections by an N=768 array of detectors.

Numerous other embodiments may be envisaged without departing from the spirit and scope of the invention.

What is claimed is:

1. A method of tracking motion present during computer tomography scan data acquisition of an object, the method comprising the steps of:

receiving a sensor time series indicative of image data of the object from a CT scanner;

providing the sensor time series to a processor; and, using the processor, comparing image data of the object acquired from identical spatial locations at different times t and t+T to obtain information about the phase of the motion of the moving object and determining a sinogram indicative of the position of the object at the time instance each image is taken.

2. A method of tracking motion present during computer tomography scan data acquisition of an object as defined in claim 1, comprising the step of band pass filtering the sinogram.

3. A method of tracking motion present during computer tomography scan data acquisition of an object as defined in claim 1, wherein the periodicity of the object motion and the periodicity of the data acquisition is not a same.

4. A method of motion correction in image data of computer tomography scans of an object comprising the steps of:

providing to a processor a sinogram indicative of the position of the object at the time instance each image is taken; and, using the processor, determining motion corrected image data from the sinogram using retrospective gating.

5. A method of motion correction in image data of computer tomography scans of an object as defined in claim 4, comprising the step of reconstructing images of the object based on the motion corrected image data.

6. A method of motion correction in image data of computer tomography scans of an object as defined in claim 4, wherein a starting point of a sinogram segment for image reconstruction is chosen in dependence upon the waveform of the sinogram.

7. A method of motion correction in image data of computer tomography scans of an object as defined in claim 6, wherein the starting point is located in a section of the sinogram having a minimum amplitude in the waveform.

8. A method of motion correction in image data of computer tomography scans of an object comprising the steps of:

providing to a processor a sinogram indicative of the position of the object at the time instance each image is taken;

using the processor:

defining a phase of interest of the sinogram;

isolating every subsequent time instance during the data acquisition period when the object is again at the pre-selected phase of its motion cycle;

selecting a number of projections at each of the time instances;

assembling the projections into a phase coherent sinogram; and, reconstructing an image of the object at the phase of interest based on the phase coherent sinogram.

9. A method of motion correction in image data of computer tomography scans of an object as defined in claim 8, wherein the subsequent time instances are isolated using sliding window correlation processing.

10. A method of motion correction in image data of computer tomography scans of an object as defined in claim 9, wherein a subset of the sinogram near the phase of interest is used as a replica and correlated with segments of the sinogram to determine a time varying correlation function.

11. A method of motion correction in image data of computer tomography scans of an object as defined in claim 10, wherein maxima of the time varying correlation function in the range of $(0.8 < CC_i \leq 1.0)$ are considered as the time instances at which the phase of interest reoccurs.

12. A method of motion correction in image data of computer tomography scans of an object as defined in claim 8, wherein missing image data are calculated using interpolation.

13. A method of motion correction in image data of computer tomography scans of an object as defined in claim 12, wherein the interpolation is based on a sliding window correlation process applied to a sinogram comprising image data acquired during one revolution of a CT scanner.

14. A method of motion correction in image data of computer tomography scans of an object as defined in claim 13, wherein the size of the windows for the correlation process is variable.

15. A method of generating a computer tomography motion picture of a moving object comprising the steps of:
   providing to a processor a sinogram indicative of the position of the object at the time instance each image is taken;
   using the processor:
      defining a number of phases of interest of the sinogram, wherein the phases of interest are equally spaced over a single motion cycle of the object;
      isolating every subsequent time instance during the data acquisition period when the object is again at the pre-selected phases of its motion cycle;
      selecting a number of projections at each of the time instances;
      assembling the projections into phase coherent sinograms; and, reconstructing an image of the object at each of the phases of interest based on the phase coherent sinograms.

16. An image data processing system for tracking motion present during computer tomography scan data acquisition of an object, the system comprising:
   a port for receiving a sensor time series indicative of image data of the object from a CT scanner; and,
   a processor for performing the steps of:
      comparing image data of the object acquired from identical spatial locations at different times t and t+T to obtain information about the phase of the motion of the moving object; and,
      determining a sinogram indicative of the position of the object at the time instance each image is taken.

17. An image data processing system for tracking motion present during computer tomography scan data acquisition of an object as defined in claim 16, wherein the processor performs the steps of:
   determining motion corrected image data from the sinogram using retrospective gating; and,
   reconstructing images of the object based on the motion corrected image data.

18. An image data processing system for tracking motion present during computer tomography scan data acquisition of an object as defined in claim 16, wherein the processor performs the steps of:
   defining a phase of interest of the sinogram;
   isolating every subsequent time instance during the data acquisition period when the object is again at the pre-selected phase of its motion cycle;
   selecting a number of projections at each of the time instances;
   assembling the projections into a phase coherent sinogram; and,
   reconstructing an image of the object at the phase of interest based on the phase coherent sinogram.

* * * * *